US011696902B2

(12) United States Patent
Somberg et al.

(10) Patent No.: US 11,696,902 B2
(45) Date of Patent: *Jul. 11, 2023

(54) METHOD OF INITIATING AND ESCALATING SOTALOL HYDROCHLORIDE DOSING

(71) Applicant: AltaThera Pharmaceuticals LLC, Chicago, IL (US)

(72) Inventors: John Somberg, Chicago, IL (US); Brandon Ira Kashfian, Chicago, IL (US); Janos Molnar, Chicago, IL (US)

(73) Assignee: AltaThera Pharmaceuticals, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/693,310

(22) Filed: Nov. 24, 2019

(65) Prior Publication Data

US 2020/0093759 A1 Mar. 26, 2020

Related U.S. Application Data

(63) Continuation-in-part of application No. 16/103,815, filed on Aug. 14, 2018, now Pat. No. 10,512,620.

(51) Int. Cl.
A61K 31/136 (2006.01)
A61K 9/19 (2006.01)
A61K 9/00 (2006.01)

(52) U.S. Cl.
CPC .......... *A61K 31/136* (2013.01); *A61K 9/0019* (2013.01); *A61K 9/0053* (2013.01)

(58) Field of Classification Search
CPC .. A61K 31/485; A61K 9/0053; A61K 31/137; A61K 31/138; A61K 31/4748
See application file for complete search history.

(56) References Cited

U.S. PATENT DOCUMENTS

| | | | |
|---|---|---|---|
| 6,043,273 A | 3/2000 | Duhaylongsod | |
| 6,060,454 A | 5/2000 | Duhaylongsod | |
| 6,101,412 A | 8/2000 | Duhaylongsod | |
| 6,124,363 A | 9/2000 | Appleby et al. | |
| 6,136,327 A | 10/2000 | Gupta et al. | |
| 6,281,246 B2 | 8/2001 | Sankaranarayanan | |
| 6,369,114 B1 | 4/2002 | Weil et al. | |
| 6,482,811 B1 | 11/2002 | Bacaner et al. | |
| 6,491,039 B1 | 12/2002 | Dobak, III | |
| 6,500,459 B1 | 12/2002 | Chhabra et al. | |
| 6,544,981 B2 | 4/2003 | Stein et al. | |
| 6,627,223 B2 | 9/2003 | Percel et al. | |
| 6,632,217 B2 | 10/2003 | Harper et al. | |
| 6,645,524 B2 | 11/2003 | Midha et al. | |
| 6,720,001 B2 | 4/2004 | Chen et al. | |
| 6,800,668 B1 | 10/2004 | Odidi et al. | |
| 6,899,700 B2 | 5/2005 | Gehling et al. | |
| 6,916,813 B2 | 7/2005 | Atwal et al. | |
| 7,004,171 B2 | 2/2006 | Benita et al. | |
| 7,005,425 B2 | 2/2006 | Belardinelli et al. | |
| 7,005,436 B2 | 2/2006 | Lloyd et al. | |
| 7,022,343 B2 | 4/2006 | Philbrook et al. | |
| 7,048,945 B2 | 5/2006 | Percel et al. | |
| 7,090,830 B2 | 8/2006 | Hale et al. | |
| 7,179,597 B2 | 2/2007 | Woosley | |
| 7,289,847 B1 | 10/2007 | Gill et al. | |
| 7,341,737 B2 | 3/2008 | Gehling et al. | |
| 7,371,254 B2 | 5/2008 | Dobak, III | |
| 7,396,524 B2 | 7/2008 | Yan | |
| 7,417,038 B1 | 8/2008 | Anker et al. | |
| 7,526,335 B2 | 4/2009 | Ferek-Petric | |
| 7,538,092 B2 | 5/2009 | Orlando et al. | |
| 7,572,776 B2 | 8/2009 | Yu et al. | |
| 7,674,820 B2 | 3/2010 | Fedida et al. | |
| 7,745,665 B2 | 6/2010 | Gant et al. | |
| 7,765,110 B1 | 7/2010 | Koneru | |
| 7,776,844 B2 | 8/2010 | Yu et al. | |
| 7,815,936 B2 | 10/2010 | Hasenzahl et al. | |
| 7,829,573 B2 | 11/2010 | Curwen et al. | |
| 7,846,968 B2 | 12/2010 | Chien et al. | |
| 7,885,824 B1 | 2/2011 | Koneru | |
| 7,885,827 B1 | 2/2011 | Koneru | |
| 7,951,183 B2 | 5/2011 | Dobak, III | |
| 8,106,099 B2 | 1/2012 | Brendel et al. | |
| 8,236,782 B2 | 8/2012 | Mosher et al. | |
| 8,263,125 B2 | 9/2012 | Vaya et al. | |
| 8,268,352 B2 | 9/2012 | Vaya et al. | |
| 8,313,757 B2 | 11/2012 | van Lengerich | |

(Continued)

FOREIGN PATENT DOCUMENTS

AU 737668 B2 8/2001
AU 765269 B2 9/2003

(Continued)

OTHER PUBLICATIONS

Thomas et al., "Rapid loading of sotalol or amiodarone for management of recent onset symptomatic atrial fibrillation: a randomized, digoxin-controlled trial," American Heart Journal, Jan. 2004. (Year: 2004).*

Barbey, J.T., et al., "Pharmacokinetic, pharmacodynamic, and safety evaluation of an accelerated dose titration regimen of sotalol in healthy middle-aged subjects," *Clin. Pharmacol. Ther.* 66(1):91-99, Mosby, Inc., United States (1999).

Ho, D.S.W., et al., "Rapid intravenous infusion of d-l sotalol: time to onset of effects on ventricular refractoriness, and safety," *European Heart Journal* 16:81-86, European Society of Cardiology, United Kingdom (1995).

(Continued)

*Primary Examiner* — Jared Barsky

(74) *Attorney, Agent, or Firm* — New River Valley IP Law, P.C.; Michele L. Mayberry

(57) ABSTRACT

This disclosure provides a method of safely and rapidly initiating or escalating oral sotalol therapy by administering an intravenous dosage of sotalol followed by oral sotalol twice daily.

5 Claims, 2 Drawing Sheets

(56) References Cited

U.S. PATENT DOCUMENTS

| | | |
|---|---|---|
| 8,377,994 B2 | 2/2013 | Gray et al. |
| 8,399,018 B2 | 3/2013 | Lichter et al. |
| 8,440,168 B2 | 5/2013 | Yang et al. |
| 8,465,769 B2 | 6/2013 | Petereit et al. |
| 8,466,277 B2 | 6/2013 | Orlando et al. |
| 8,575,348 B2 | 11/2013 | Rao et al. |
| 8,696,696 B2 | 4/2014 | Solem |
| 8,709,076 B1 | 4/2014 | Matheny et al. |
| 8,753,674 B2 | 6/2014 | Helson |
| 8,828,432 B2 | 9/2014 | van Lengerich |
| 8,865,213 B2 | 10/2014 | Sheth et al. |
| 8,871,452 B2 | 10/2014 | Lee |
| 8,906,847 B2 | 12/2014 | Cleemann et al. |
| 8,962,574 B2 | 2/2015 | Reilly |
| 8,987,262 B2 | 3/2015 | Leaute-Labreze et al. |
| 9,011,526 B2 | 4/2015 | Matheny |
| 9,016,221 B2 | 4/2015 | Brennan et al. |
| 9,044,319 B2 | 6/2015 | Matheny |
| 9,060,969 B2 | 6/2015 | Matheny |
| 9,078,929 B2 | 7/2015 | Kuebelbeck et al. |
| 9,161,952 B2 | 10/2015 | Matheny et al. |
| 9,239,333 B2 | 1/2016 | Snider |
| 9,255,104 B2 | 2/2016 | Rao et al. |
| 9,308,084 B2 | 4/2016 | Matheny |
| 9,399,067 B2 | 7/2016 | Mosher et al. |
| 9,474,719 B2 | 10/2016 | Mullen et al. |
| 9,498,481 B2 | 11/2016 | Rao et al. |
| 9,549,912 B2 | 1/2017 | Milner et al. |
| 9,554,989 B2 | 1/2017 | Kaplan et al. |
| 9,585,851 B2 | 3/2017 | Yun et al. |
| 9,585,884 B2 | 3/2017 | Rao et al. |
| 9,597,302 B1 | 3/2017 | Yan et al. |
| 9,616,026 B2 | 4/2017 | Singh |
| 9,682,041 B2 | 6/2017 | Helson |
| 9,724,297 B2 | 8/2017 | Thomas et al. |
| 9,770,514 B2 | 9/2017 | Ghebre-Sellassie et al. |
| 9,889,148 B2 | 2/2018 | Daemmgen et al. |
| 9,995,756 B2 | 6/2018 | Saffitz et al. |
| 10,117,881 B2 | 11/2018 | Helson |
| 10,238,602 B2 | 3/2019 | Helson et al. |
| 10,258,691 B2 | 4/2019 | Helson et al. |
| 10,349,884 B2 | 7/2019 | Helson et al. |
| 10,357,458 B2 | 7/2019 | Helson |
| 10,449,193 B2 | 10/2019 | Helson et al. |
| 10,450,267 B2 | 10/2019 | Stancl |
| 10,512,620 B1 | 12/2019 | Somberg et al. |
| 10,537,588 B2 | 1/2020 | Daemmgen et al. |
| 10,603,316 B2 | 3/2020 | Xiong et al. |
| 10,617,639 B2 | 4/2020 | Helson |
| 10,793,519 B2 | 10/2020 | Somberg et al. |
| 10,799,138 B2 | 10/2020 | Ivaturi et al. |
| 10,888,524 B2 | 1/2021 | Yenkar et al. |
| 10,888,552 B2 | 1/2021 | Rothman |
| 11,286,235 B2 | 3/2022 | Somberg et al. |
| 11,344,518 B2 | 5/2022 | Somberg |
| 11,610,660 B1 | 3/2023 | Devlin et al. |
| 2007/0009564 A1 | 1/2007 | McClain et al. |
| 2007/0009654 A1 | 1/2007 | McClain et al. |
| 2012/0003318 A1 | 1/2012 | Schuler et al. |
| 2014/0235631 A1 | 8/2014 | Bunt et al. |
| 2014/0276404 A1 | 9/2014 | Orlowski |
| 2015/0081010 A1 | 3/2015 | Matheny |
| 2015/0210712 A1 | 7/2015 | Blumberg et al. |
| 2016/0082159 A1 | 3/2016 | Orlowski |
| 2016/0128944 A1 | 5/2016 | Chawrai et al. |
| 2016/0228379 A1 | 8/2016 | Kumar et al. |
| 2016/0271070 A1 | 9/2016 | Singh et al. |
| 2016/0271157 A1 | 9/2016 | Ahmed et al. |
| 2016/0303133 A1 | 10/2016 | Dudley et al. |
| 2016/0317388 A1 | 11/2016 | Bhargava et al. |
| 2017/0049705 A1 | 2/2017 | Mateescu et al. |
| 2017/0087105 A1 | 3/2017 | Yan et al. |
| 2017/0100387 A1 | 4/2017 | Arora et al. |
| 2017/0119627 A1 | 5/2017 | Bhargava et al. |
| 2017/0157076 A1 | 6/2017 | Yacoby-Zeevi et al. |
| 2017/0231885 A1 | 8/2017 | Cremers et al. |
| 2017/0258781 A1 | 9/2017 | Noujaim et al. |
| 2017/0296493 A1 | 10/2017 | Thomas et al. |
| 2017/0348303 A1 | 12/2017 | Bosse et al. |
| 2018/0071390 A1 | 3/2018 | Patel et al. |
| 2019/0307343 A1* | 10/2019 | Ivaturi ............... A61B 5/4839 |
| 2019/0352257 A1 | 11/2019 | Somberg et al. |
| 2019/0380605 A1 | 12/2019 | Ivaturi et al. |
| 2019/0388371 A1 | 12/2019 | Somberg |
| 2019/0389888 A1 | 12/2019 | McChesney et al. |
| 2020/0085771 A1 | 3/2020 | Somberg et al. |
| 2020/0226481 A1 | 7/2020 | Sim et al. |
| 2020/0253903 A1 | 8/2020 | Somberg |
| 2020/0338027 A1 | 10/2020 | Somberg |
| 2020/0383941 A1 | 12/2020 | Brelidze et al. |
| 2021/0076959 A1 | 3/2021 | Ivaturi et al. |
| 2021/0107867 A1 | 4/2021 | Somberg et al. |
| 2021/0283049 A1 | 9/2021 | Somberg |
| 2021/0346325 A1 | 11/2021 | Somberg |
| 2022/0142954 A1 | 5/2022 | Somberg |
| 2022/0241225 A1 | 8/2022 | Somberg |
| 2022/0339130 A1 | 10/2022 | Somberg et al. |
| 2023/0075398 A1 | 3/2023 | Devlin et al. |

FOREIGN PATENT DOCUMENTS

| | | |
|---|---|---|
| AU | 2003233653 A1 | 12/2003 |
| AU | 2005299693 A1 | 5/2006 |
| AU | 2010231494 A1 | 11/2011 |
| AU | 2013203252 A1 | 8/2013 |
| AU | 2013381856 A1 | 7/2015 |
| AU | 2011289176 B2 | 9/2015 |
| AU | 2016266020 B2 | 10/2018 |
| AU | 2017357916 A1 | 5/2019 |
| AU | 2016313439 B2 | 10/2019 |
| AU | 2015269699 B2 | 8/2020 |
| EP | 0898964 A1 | 3/1999 |
| EP | 1027329 B1 | 2/2003 |
| EP | 1467705 A2 | 10/2004 |
| EP | 1474105 A2 | 11/2004 |
| EP | 1605976 A1 | 12/2005 |
| EP | 2429291 A1 | 3/2012 |
| EP | 1501467 B1 | 5/2012 |
| EP | 2238127 B1 | 8/2012 |
| EP | 2238128 B1 | 8/2012 |
| EP | 2228065 B1 | 12/2012 |
| EP | 2797556 A1 | 11/2014 |
| EP | 2861254 A2 | 4/2015 |
| EP | 3100728 A1 | 12/2016 |
| EP | 2999461 A4 | 2/2017 |
| EP | 2714011 B1 | 1/2018 |
| EP | 1951210 B1 | 12/2018 |
| WO | 9921829 A1 | 5/1999 |
| WO | 03020240 A2 | 3/2003 |
| WO | 03059318 A2 | 7/2003 |
| WO | 2004082716 A1 | 9/2004 |
| WO | 2007053393 A2 | 5/2007 |
| WO | 2010132711 A1 | 11/2010 |
| WO | 2012167212 A3 | 2/2013 |
| WO | 2013185764 A2 | 12/2013 |
| WO | 2014133539 A1 | 9/2014 |
| WO | 2014143108 A1 | 9/2014 |
| WO | 2014186843 A1 | 11/2014 |

OTHER PUBLICATIONS

Läer, S., et al., "Development of a safe and effective pediatric dosing regimen for sotalol based on population pharmacokinetics and pharmacodynamics in children with supraventricular tachycardia," *J. American College of Cardiology* 46(7):1322-1330, Elsevier, Inc., United States (2005).

Lynch, J. J., et al., "Prevention of ventricular fibrillation by dextrorotatory sotalol in a conscious canine model of sudden coronary death," *American Heart Journal* 109(5):949-958, Elsevier, Inc., United States (1985).

Neumar, R.W., et al., "Part 8: Adult Advanced Cardiovascular Life Support," *Circulation* 122(3):S729-S767 (2010).

(56) References Cited

OTHER PUBLICATIONS

Snider, M., et al., "Initial experience with antiarrhythnuc medication monitoring by clinical pharmacists in an outpatient setting: a retrospective review," Clinical Therapeutics 31(6):1209-1218, Excerpta Medica, Inc., United States (2009).
Somberg, J.C., et al., "Developing a Safe Intravenous Sotalol Dosing Regimen," American Journal of Therapeutics 17:365-372, Lippincott Williams & Wilkins, United States (2010).
Somberg, J.C., et al., "Gender Differences in Cardiac Repolarization Following Intravenous Sotalol Administration," J. Cardiovasc. Pharmacol. Ther. 17(1):86-92, Sage, United States (2012).
Yarlagadda, B., et al., "Safety and Efficacy of Inpatient Initiation of Dofetilide Versus Sotalol for Atrial Fibrillation," J. Atrial Fibrillation 10(4):1805, Cardiofront, United States (2017).
El-Assaad, I., et al., "Lone Pediatric Atrial Fibrillation in the United States: Analysis of Over 1500 Cases," Pediatr. Cardiol. 38:1004-1009, Springer Publishing, United States (2017).
Galloway, C.D., et al., "Development and Validation of a Deep-Learning Model to Screen for Hyperkalemia From the Electrocardiogram," JAMA Cardiol.: E1-E9, American Medical Association, United States (Apr. 3, 2019).
Hannun, A.Y., et al., "Cardiologist-level arrhythmia detection and classification in ambulatory electrocardiograms using a deep neural network," Nature Medicine 25:65-69, Nature Publishing, United States (Jan. 2019).
Marill, K.A., et al., "Meta-analysis of the Risk of Torsades de Pointes in Patients Treated with Intravenous Racemic Sotalol," Academic Emergency Medicine 8(2):117-124, Wiley, United States (2001).
Peters, F.P.J., et al., "Treatment of recent onset atrial fibrillation with intravenous solalol and/or flecainide," Netherlands Journal of Medicine 53:93-96, Elsevier Science B.V., Netherlands (1998).
Radford, D.J., et al., "Atrial Fibrillation in Children," Pediatrics 59(2):250-256, American Academy of Pediatrics, United States (1977).
Thomas, S.P., et al., "Rapid loading of sotalol or amiodarone for management of recent onset symptomatic atrial fibrillation: A randomized, digoxin-controlled trial," Am. Heart J. 147:e3 (6 pages), Elsevier Inc., Netherlands (2004).
U.S. Appl. No. 16/376,706, filed Apr. 5, 2019, U.S. Patent and Trademark Office, Alexandria, VA [unpublished].
Li et al., "Efficacy of Intravenous Sotalol for Treatment of Incessant Tacharrhythmias in Children," Am J Cardiol 2017; 119: 1366-1370.
Saul et al., "Pharmacokinetics and pharmacodynamics of sotalol in a pediatric population with superventricular and ventricular tacharrhythmia," Clinical Pharmacology and Therapeutics, Mar. 2001.
Batul et al., "Intravenous Sotalol-Reintroducing a Forgotten Agent to the Electrophysiology Therapeutic Arsenal," Journal of Atrial Firbillation, Feb.-Mar. 2017, vol. 9, Issue 5.
Gomes, J.A., "Oral d,l Sotalol reduces the incidence of postoperative atrial fibrillation in coronary artery bypass surgery patients: a randomized, double-blind, placebo-controlled study," J. Am. Coll. Cardio. 34(2):334-9 (1999).
Hoffman et al. "Renal Insufficiency and Medication in Nursing Homes" Medicine Deutsches Arzteblatt International 2016; 113: 92-98.
Kerin, Nicholas A., "Intravenous Sotalol: an under used treatment strategy," Cardiology (2018) 140:143-145.
Li, X., "Pediatric dosing of intravenous sotalol based on body surface area in patients with arrhythmia," Pediatr Cardiol (2017) 38:1450-1455.
Patel, A., "Is Sotalol more effective than standard beta-blockers for prophylaxis of atrial fibrillation during cardiac surgery?" Interactive Cardiovascular and Thoracic Surgery 4 (2005) 147-50.
Peters, N.S., "Post-cardioversion atrial fibrillation: the synthesis of modern concepts?" european Heart J. (2000) 21, 1119-1121.
Sanjuan, R., "Preoperative use of sotalol versus atenolol for atrial fibrillation after cardiac surgery," Ann Thorac Surg (2004) 77:838-43.
Somberg, J.C., "QT prolongation and serum sotalol concentration are highly correlated following intravenous and oral sotalol," Cardiology (2010) 116(3):219-25.
Somberg, John et al. Model-Informed Development of Sotalol Loading and Dose Escalation Employing an Intravenous Infusion. Cardiol Res. 2020;11(5):294-304.
Sundquist, H.K. et al., "Serum levels and half-life of sotalol in chronic renal failure", Annals of Clinical Research, Dec. 1, 1975, 7(6), Abstract Only.
Tse, H.F., "Atrial pacing for suppression of early reinitiation of atrial fibrillation after successful internal cardioversion," european Heart J. (2000) 21, 1167-1176.
U.S. Appl. No. 16/376,706 (U.S. Pat. No. 10,799,138), file history Dec. 2020, 151 pages.
Valdes, S.O., "early experience with intravenous sotalol in children with and without congenital heart disease," Heart Rhythm 15(12): 1862-1869, Elsevier Inc., (Jul. 9, 2018).
Devlin, Jodi) Co-pending U.S. Appl. No. 17/566,840, filed Dec. 31, 2021, Specification, Claims, and Figures.
Ivaturi, Vijay et al.) U.S. Appl. No. 16/549,620, filed Aug. 23, 2019, Specification, Claims, Figures and File History as of Dec. 2020, 77 pages (abandoned).
Ivaturi, Vijay et al.) U.S. Appl. No. 17/003,297, filed Aug. 26, 2020, Specification, Claims, Figures.
Somberg, John C. et al.) Co-Pending U.S. Appl. No. 16/103,815, filed Aug. 14, 2018, Specification, Claims, Figures.
Somberg, John C. et al.) Co-Pending U.S. Appl. No. 16/693,312, filed Nov. 24, 2019, Specification, Claims, Figures.
Somberg, John C. et al.) Co-Pending U.S. Appl. No. 16/726,361, filed Dec. 24, 2019, Specification, Claims, Figures.
Somberg, John) Co-Pending U.S. Appl. No. 16/849,099, filed Apr. 15, 2020, Specification and Claims.
Somberg, John) Co-Pending U.S. Appl. No. 16/863,567, filed Apr. 30, 2020, Specification and Claims.
Somberg, John) Co-Pending U.S. Appl. No. 16/946,941, filed Jul. 13, 2020, Specification and Claims.
Somberg, John) Co-Pending U.S. Appl. No. 17/306,490, filed May 3, 2021, Specification and Claims.
Somberg, John) Co-Pending U.S. Appl. No. 17/585,190, filed Jan. 26, 2022, Specification and Claims.
U.S. Appl. No. 17/003,297, Preliminary Amendment filed Dec. 8, 2020, 9 pages.
Blair, Andrew D., et al., Sotalol kinetics in renal insufficiency, Clin. Pharmacol. Ther., 457-463 (Apr. 1981) (7 pages).
Campbell, T.J., "Intravenous sotalol for the treatment of atrial fibrillation and flutter after cardiopulmonary bipass comparison with disopyramide and digoxin in a randomised trial," BR Heart J. (1985) 54:86-90.
Co-Pending U.S. Appl. No. 16/103,815, Final Office Action dated Aug. 13, 2019, 13 pages.
Co-Pending U.S. Appl. No. 16/103,815, Non-Final Office Action dated Feb. 6, 2019, 9 pages.
Co-Pending U.S. Appl. No. 16/103,815, Notice of Allowance dated Oct. 30, 2019, 12 pages.
Co-Pending U.S. Appl. No. 16/103,815, Response to Aug. 13, 2019 Final Office Action, filed Oct. 17, 2019, 10 pages.
Co-Pending U.S. Appl. No. 16/103,815, Response to Dec. 13, 2018 Restriction Requirement, filed Dec. 31, 2018, 3 pages.
Co-Pending U.S. Appl. No. 16/103,815, Response to Feb. 6, 2019 Non-Final Office Action, filed May 6, 2019, 17 pages.
Co-Pending U.S. Appl. No. 16/103,815, Restriction Requirement dated Dec. 13, 2018, 6 pages.
Co-Pending U.S. Appl. No. 16/376,706, Final Office Action dated Mar. 27, 2020, 12 pages.
Co-Pending U.S. Appl. No. 16/376,706, Non-final Office Action dated Nov. 12, 2019, 12 pages.
Co-Pending U.S. Appl. No. 16/376,706, Notice of Allowance and Examiner Initiated Interview Summary dated Jun. 10, 2020, 8 pages.
Co-Pending U.S. Appl. No. 16/376,706, Response to Mar. 27, 2020 Final Office Action dated May 27, 2020, 11 pages.
Co-Pending U.S. Appl. No. 16/376,706, Response to Nov. 12, 2019 Non-Final Office Action filed Feb. 12, 2020, 10 pages.

(56) References Cited

OTHER PUBLICATIONS

Co-Pending U.S. Appl. No. 16/693,312, Final Office Action dated Mar. 29, 2021, 14 pages.
Co-Pending U.S. Appl. No. 16/693,312, Non-Final Office Action dated Jan. 7, 2022, 15 pages.
Co-Pending U.S. Appl. No. 16/693,312, Non-Final Office Action dated Oct. 20, 2020, 17 pages.
Co-Pending U.S. Appl. No. 16/693,312, Response to Mar. 29, 2021 Final Office Action, filed Sep. 29, 2021, 13 pages.
Co-Pending U.S. Appl. No. 16/693,312, Response to Oct. 20, 2020 Non-Final Office Action, filed Feb. 22, 2021, 11 pages.
Co-Pending U.S. Appl. No. 16/849,099, Final Office Action dated Feb. 3, 2021, 24 pages.
Co-Pending U.S. Appl. No. 16/849,099, Non-Final Office Action dated Jul. 9, 2020, 19 pages.
Co-Pending U.S. Appl. No. 16/849,099, Notice of Abandonment, filed Aug. 20, 2021, 2 pages.
Co-Pending U.S. Appl. No. 16/849,099, Response to Jul. 9, 2020 Non-Final Office Action, dated Dec. 9, 2020, 10 pages.
Co-Pending U.S. Appl. No. 16/863,567, Advisory Action dated Dec. 30, 2021, 11 pages.
Co-Pending U.S. Appl. No. 16/863,567, Final Office Action dated Dec. 28, 2020, 17 pages.
Co-Pending U.S. Appl. No. 16/863,567, Final Office Action dated Oct. 26, 2021, 11 pages.
Co-Pending U.S. Appl. No. 16/863,567, Non-Final Office Action and Examiner Initiated Interview Summary dated Jun. 9, 2021, 14 pages.
Co-Pending U.S. Appl. No. 16/863,567, Non-Final Office Action dated Jun. 4, 2020, 18 pages.
Co-Pending U.S. Appl. No. 16/863,567, Response to Jun. 4, 2020 Non-Final Office Action dated Dec. 4, 2020, 10 pages.
Co-Pending U.S. Appl. No. 16/863,567, Response to Jun. 9, 2021 Non-Final Office Action dated Oct. 12, 2021, 8 pages.
Co-Pending U.S. Appl. No. 16/863,567, Response to May 13, 2020 Restriction Requirement, filed May 26, 2020, 44 pages.
Co-Pending U.S. Appl. No. 16/863,567, Response to Oct. 26, 2021 Final Office Action, dated Dec. 10, 2021, 8 pages.
Co-Pending U.S. Appl. No. 16/863,567, Restriction Requirement dated May 13, 2020, 5 pages.
Co-Pending U.S. Appl. No. 16/946,941, Preliminary Amendment filed Jan. 20, 2021, 3 pages.
Dahmane, E., "Clinical Pharmacology-Driven Research to Optimize Bedside Therapeutics of Sotalol Therapy," Clin Transl Sci (2019) 12:648-656.
Dumas, M. et al., "Variations of sotalol kinetics in renal insufficiency", International Journal of Clinical Pharmacology, Therapy, and Toxicology, Oct. 1, 1989, 27(10), Abstract only.
FDA Highlights of Prescribing Information sotalol hydrochloride injection (2009), https://www.accessdata.fda.gov/drugsatfda_docs/label/2009/022306s000lbl.pdf.
FDA Highlights of Prescribing Information Sotylize (sotalol hydrochloride (2014), https://www.accessdata.fda.gov/drugsatfda_docs/label/2014/205108s000lbl.pdf.
Ivaturi, Vijay et al.) U.S. Appl. No. 18/156,092, filed Jan. 18, 2023, Specification, Claims, Figures.
Kashfian, Brandon Ira et al.) Co-Pending U.S. Appl. No. 17/892,301, filed Aug. 22, 2022, Specification and Claims.
Somberg, John C. et al.) Co-Pending U.S. Appl. No. 17/861,226, filed Jul. 10, 2022, Specification, Claims, Figures.
Somberg, John) Co-Pending U.S. Appl. No. 17/725,189, filed Apr. 20, 2022, Specification and Claims.
U.S. Appl. No. 17/003,297, Final Office Action dated Jul. 27, 2022, 16 pages.
U.S. Appl. No. 17/003,297, Non-Final Office Action dated Mar. 14, 2022, 14 pages.
U.S. Appl. No. 17/003,297, Notice of Allowance dated Oct. 18, 2022, 7 pages.
U.S. Appl. No. 17/003,297, Response to Final Office Action dated Sep. 27, 2022, 12 pages.
U.S. Appl. No. 17/003,297, Response to Mar. 14, 2022 Non-Final Office Action, dated Jun. 15, 2022, 12 pages.
Batra, Anjan S., et al., "Junctional ectopic tachycardia: Current strategies for diagnosis and management," Progress in Pediatric Cardiology, 35 (2013) 49-54.
Borquez, Alejandro A., et al., "Intravenous Sotalol in the Young, Safe and Effective Treatment With Standardized Protocols," JACC: Clinical Elecrophysiology, vol. 6, No. 4, Apr. 2020:425-32 (2020).
Cantillon, D. J. and Amuthan, R. "Atrial Fibrillation", Cleveland Clinic: Center for Continuing Education, Disease Management: https://www.clevelandclinicmeded.com/medicalpubs/diseasemanagement/cardiology/atrial-fibrillation/, Aug. 2018, 18 pages.
CHOC Children's, "Junctional Ectopic Tachycardia (JET) Care Guideline for Cardiovascular Intensive Care Unit (CVICU)," Sep. 18, 2019.
Cilliers, Antionette M., et al., "Junctional ectopic tachycardia in six paediatric patients," Heart; 78:413-415 (1997).
Co-Pending U.S. Appl. No. 16/693,312, Final Office Action dated Oct. 14, 2022, 16 pages.
Co-Pending U.S. Appl. No. 16/693,312, Response to Jan. 7, 2022 Non-Final Office Action, dated Jul. 6, 2022, 8 pages.
Co-Pending U.S. Appl. No. 16/946,941, Non-Final Office Action dated Feb. 7, 2022, 15 pages.
Co-Pending U.S. Appl. No. 16/946,941, Notice of Allowance dated Apr. 4, 2022, 9 pages.
Co-Pending U.S. Appl. No. 16/946,941, Response to Feb. 7, 2022 Non-Final Office Action, dated Mar. 8, 2022, 6 pages.
Co-Pending U.S. Appl. No. 17/306,490, Preliminary Amendment filed Dec. 7, 2022, 38 pages.
Co-Pending U.S. Appl. No. 17/566,840, Non-Final Office Action dated Mar. 23, 2022, 11 pages.
Co-Pending U.S. Appl. No. 17/566,840, Notice of Allowance dated Jul. 25, 2022, 7 pages.
Co-Pending U.S. Appl. No. 17/566,840, Notice of Allowance dated Nov. 9, 2022, 7 pages.
Co-Pending U.S. Appl. No. 17/566,840, Petition Under 37 CFR 1.181 and Preliminary Amendment, dated Feb. 22, 2022, 9 pages.
Co-Pending U.S. Appl. No. 17/566,840, Response to Mar. 23, 2022 Non-Final Office Action, dated Jul. 7, 2022, 10 pages.
Co-Pending U.S. Appl. No. 17/585,190, Preliminary Amendment dated Mar. 4, 2022, 4 pages.
Co-Pending U.S. Appl. No. 17/861,226, Preliminary Amendment dated Jul. 10, 2022, 4 pages.
FDA "Highlights of Prescribing Information" for sotalol hydrochloride injection, Revised Mar. 2020, 16 pages, https://www.accessdata.fda.gov/drugsatfda_docs/label/2020/022306s005lblrpl.pdf.
Le Coz, F. et al. Pharmacokinetic and pharmacodynamic modeling of the effects of oral and intravenous administrations of dofetilide on ventricular repolarization. Clin Pharmacol Ther 1995; 57:533.
Learn the Heart, "Antiarrhythmic Drug Review," https://www.healio.com/cardiology/learn-the-heart/cardiology-review/topic-reviews/antiarrhythmic-drugs (Year: 2022).
Maragnes, P., et al., "Usefulness of oral sotalol for the treatment of junctional ectopic tachycardia," Int'l J. of Cardiology, 35 (1995) 165-167.
Rasmussen, H.S. et al., Dofetilide, A Novel Class III Antiarrhythmic Agent, J Cardiovasc Pharmacol. 1992;20 Suppl 2:S96-105.
Rosseau, M. F., Cardiac and Hemodynamic Effects of Intravenous Dofetilide in Patients With Heart Failure, Am J Cardiol 2001;87:1250-1254.
Sedgwick, M. et al., Pharmacokinetic and pharmacodynamic effects of UK-68,798, a new potential class III antiarrhythmic drug, Br. J. Clin. Pharmac. (1991), 31, 515-519.
Somberg, et al., "Sotalol versus Amiodarone in Treatment of Atrial Fibrillation," J. Atrial Fibrillation, Feb.-Mar. 2016, vol. Issue 5.
(Devlin, Jodi) Co-pending U.S. Appl. No. 18/121,980, filed Mar. 15, 2023, Specification, Claims, and Figures.
(Kashfian, Brandon Ira) Co-Pending U.S. Appl. No. 18/126,561, filed Mar. 27, 2023, Specification and Claims.
(Kashfian, Brandon Ira) Co-Pending U.S. Appl. No. 18/135,467, filed Apr. 17, 2023, Specification and Claims.
(Kashfian, Brandon Ira) Co-Pending U.S. Appl. No. 18/304,196, filed Apr. 20, 2023, Specification and Claims.

(56) References Cited

OTHER PUBLICATIONS (Kashfian, Brandon Ira) Co-Pending U.S. Appl. No. 18/306,660, filed Apr. 25, 2023, Specification and Claims.
(Kashfian, Brandon Ira) Co-Pending U.S. Appl. No. 18/315,790, filed May 11, 2023, Specification and Claims.
(Kashfian, Brandon Ira) Co-Pending U.S. Appl. No. 18/321,220, filed May 22, 2023, Specification and Claims.
Co-Pending U.S. Appl. No. 16/693,312, Response to Oct. 14, 2022 Final Office Action dated Apr. 14, 2023, 16 pages.

* cited by examiner

METHOD OF INITIATING AND ESCALATING SOTALOL HYDROCHLORIDE DOSING

FIELD

This disclosure provides methods of treating or preventing atrial fibrillation, atrial flutter, or a combination thereof comprising intravenously administering sotalol hydrochloride to subject in need thereof.

BACKGROUND

Sotalol hydrochloride ("sotalol") is Vaughan Williams Class III anti-arrhythmic drug that prolongs cardiac action potential duration by blocking the outward potassium channel IKr (rapid potassium rectifier current), thereby prolonging repolarization time.

Although sotalol is effective at treating or preventing atrial fibrillation, atrial flutter, and combinations thereof, sotalol's mechanism of action is both anti-arrhythmic and pro-arrhythmic. Too much sotalol too fast can lead to excessive prolongation of repolarization time giving rise to life threatening arrhythmias, especially Torsade de Pointes ventricular tachycardia (Tdp). Thus, it is well understood in the art, that during sotalol's initial loading, or in a dose escalation intervention, it is critical to monitor a subject's QTc interval to avoid excessive QTc prolongation.

Due to sotalol's potential to induce arrhythmia, the FDA has mandated in-hospital QTc monitoring for at least three days upon initial sotalol hydrochloride loading and for dose escalation. Although this extended hospital stay is effective at reducing subject risk, maintaining the subject in a telemetry unit for three days is extremely expensive, making sotalol a less desirable treatment choice in a managed care environment. A need therefore exists to develop methods of reducing the length of hospital stay required to safely and efficaciously administer sotalol to subjects in need thereof.

BRIEF SUMMARY

The present disclosure provides methods of safely intravenously administering sotalol hydrochloride to subjects in need thereof over a significantly reduced period of time, such as about 1 hour. In particular, the present disclosure provides a method of achieving a sotalol steady state $C_{max}$ after about 1 hour of intravenous administration equal to the sotalol steady state $C_{max}$ typically achieved after BID PO sotalol administration for three days.

In one embodiment, this disclosure provides a method of treating or preventing atrial fibrillation, atrial flutter, or a combination thereof in a subject in need thereof, the method comprising intravenously administering to the subject between about 0.825 mg/min and about 1.17 mg/min of sotalol hydrochloride over a period of about 60 minutes.

In some embodiments, the method further comprises discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

In some embodiments, the intravenous administration of sotalol hydrochloride results in a sotalol steady state $C_{max}$ of between about 750 ng/mL and about 850 ng/mL in the subject.

In some embodiments, the method further comprises orally administering to the subject 80 mg of sotalol hydrochloride between about 1 hour and about 6 hours after completion of the intravenous administration.

In some embodiments, the method further comprises discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

In some embodiments, the method further comprises initiating an oral BID administration regimen of sotalol hydrochloride when the subject has a QTc interval at between about 2 hours and about 3 hours after oral administration of sotalol hydrochloride that is less than or equal to 500 msec; or wherein the subject has a ΔQTc that is less than 20% of the subject's QTc prior to intravenous sotalol administration.

Also provided is a method of treating or preventing atrial fibrillation, atrial flutter, or a combination thereof in a subject in need thereof, the method comprising intravenously administering to the subject between about 1.23 mg/min and about 1.76 mg/min of sotalol hydrochloride over a period of about 60 minutes.

In some embodiments, the method further comprises discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

In some embodiments, the intravenous administration of sotalol hydrochloride results in a sotalol steady state $C_{max}$ of between about 1150 ng/mL and about 1250 ng/mL in the subject.

In some embodiments, the method further comprises orally administering to the subject 120 mg of sotalol hydrochloride between about 1 hour and about 6 hours after completion of the intravenous administration.

In some embodiments, the method further comprises discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

In some embodiments, the method further comprises initiating an oral BID administration regimen of sotalol hydrochloride when the subject has a QTc interval at between about 2 hours and about 3 hours after oral administration of sotalol hydrochloride that is less than or equal to 500 msec; or wherein the subject has a ΔQTc that is less than 20% of the subject's QTc prior to intravenous sotalol administration.

Also provided is a method of treating atrial fibrillation, atrial flutter, or a combination thereof in a subject in need thereof, the method comprising intravenously administering to the subject between about 1.65 mg/min to about 2.35 mg/min of sotalol hydrochloride over a period of about 60 minutes.

In some embodiments, the method further comprises discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

In some embodiments, the intravenous administration of sotalol hydrochloride results in a sotalol steady state $C_{max}$ of between about 1550 ng/mL and about 1650 ng/mL in the subject.

In some embodiments, the method further comprises orally administering to the subject 160 mg of sotalol hydrochloride between about 1 hour and about 6 hours after completion of the intravenous administration.

In some embodiments, the method further comprises discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

In some embodiments, the method further comprises initiating an oral BID administration regimen of sotalol hydrochloride when the subject has a QTc interval at between about 2 hours and 3 hours after oral administration of sotalol hydrochloride that is less than or equal to 500 msec; or wherein the subject has a ΔQTc that is less than 20% the subject's QTc prior to intravenous sotalol administration.

Also provided is a method of treating or preventing atrial fibrillation, atrial flutter, or a combination thereof in a subject in need thereof, the method comprising intravenously administering to the subject between about 0.825 mg/min and about 1.17 mg/min of sotalol hydrochloride over a period of about 60 minutes, wherein the subject received an administration of sotalol hydrochloride between about 12 hours and about 24 hours before the intravenous administration.

In some embodiments, the subject received an oral administration of 80 mg of oral sotalol hydrochloride between about 12 and about 24 hours before the intravenous administration.

In some embodiments, the method further comprises discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

In some embodiments, the intravenous administration of sotalol hydrochloride results in a sotalol steady state $C_{max}$ of between about 1150 ng/mL and about 1250 ng/mL in the subject.

In some embodiments, the method further comprises orally administering to the subject 120 mg of sotalol hydrochloride between about 1 hour and about 6 hours after completion of the intravenous administration.

In some embodiments, the method further comprises discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

In some embodiments, the method further comprises initiating an oral BID administration regimen of sotalol hydrochloride when the subject has a QTc interval at between about 2 hours and 3 hours after oral administration of sotalol hydrochloride that is less than or equal to 500 msec; or wherein the subject has a ΔQTc that is less than 20% the subject's QTc prior to intravenous sotalol administration.

Also provided is a method of treating or preventing atrial fibrillation, atrial flutter, or a combination thereof in a subject in need thereof, the method comprising intravenously administering to the subject between about 1.05 mg/min and 1.47 mg/min of sotalol hydrochloride over a period of about 60 minutes, wherein the subject received an administration of sotalol hydrochloride between about 12 hours and about 24 hours before the intravenous administration.

In some embodiments, the subject received an oral administration of 120 mg of oral sotalol hydrochloride between about 12 and about 24 hours before the intravenous administration.

In some embodiments, the method further comprises discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

In some embodiments, the intravenous administration of sotalol hydrochloride results in a sotalol steady state $C_{max}$ of between about 1550 ng/mL and about 1650 ng/mL in the subject.

In some embodiments, the method further comprises orally administering to the subject 160 mg of sotalol hydrochloride between about 1 hour and about 6 hours after completion of the intravenous administration.

In some embodiments, the method further comprises discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

In some embodiments, the method further comprises initiating an oral BID administration regimen of sotalol hydrochloride when the subject has a QTc interval at between about 2 hours and 3 hours after oral administration of sotalol hydrochloride that is less than or equal to 500 msec; or wherein the subject has a ΔQTc that is less than 20% the subject's QTc prior to intravenous sotalol administration.

BRIEF DESCRIPTION OF THE DRAWINGS

The above-mentioned features and objects of this disclosure will become more apparent with reference to the following description taken in conjunction with the accompanying drawings.

DETAILED DESCRIPTION

Definitions

Figure 1:
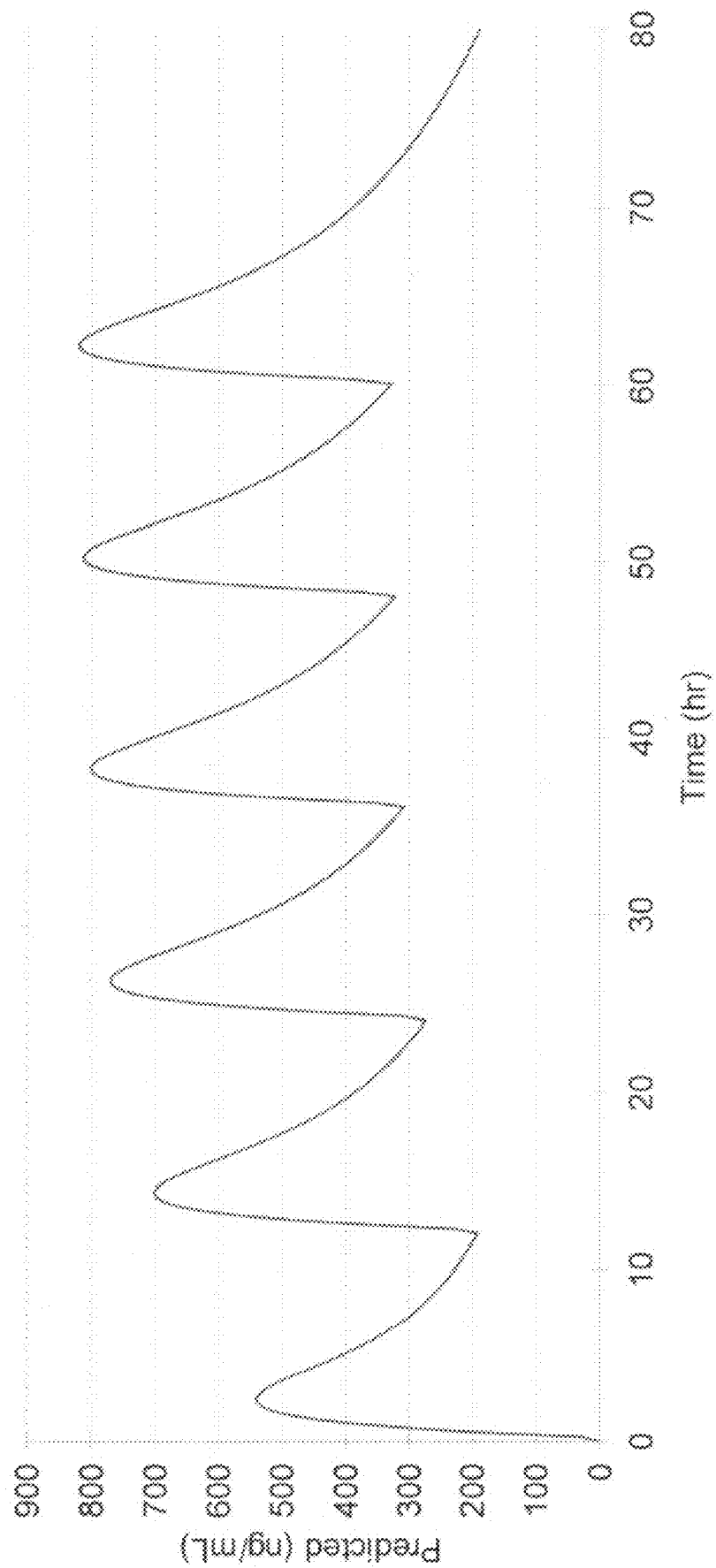
FIG. 1 is a line graph depicting initiation of an intravenous dose of 55 mg of sotalol hydrochloride to achieve an estimated steady state $C_{max}$ equivalent to the steady state $C_{max}$ achieved via chronic oral twice daily dosing of 80 mg sotalol hydrochloride in a subject with normal renal function.

As used in this disclosure, the term "or" is defined as a logical disjunction (i.e., and/or) and does not indicate an exclusive disjunction unless expressly indicated as such with the terms "either," "unless," "alternatively," and words of similar effect.

As used herein, the term "about" means +/−10% of the value specified. By way of example only, "about 50" means from 45 to 55.

The term "$C_{max}$" refers to the maximum blood concentration shown on the curve that represents changes in blood concentrations of an active pharmaceutical ingredient (e.g., sotalol hydrochloride), or a metabolite of the active pharmaceutical ingredient, over time.

The term "steady state $C_{max}$" refers to the state, wherein the post dose maximum plasma concentration of sotalol hydrochloride does not differ from one dose to another. In some embodiments, the method described herein provides a steady state $C_{max}$ of sotalol hydrochloride concentration in a range between about 800 ng/mL and about 1600 ng/mL, depending upon the amount of sotalol dosed.

The term "QT" refers to a telltale measurement seen on an electrocardiogram (ECG). The QT interval is measured from the start of the Q wave or the QRS complex, to the end of the T wave, where the Q wave corresponds to the beginning of ventricular depolarization and the T wave end corresponds to the end of ventricular repolarization.

The term "QTc" refers to a calculated interval that represents the QT interval corrected for heart rate. The QTc interval may be derived by simple mathematical correlation of the QT interval and the heart rate. In preferred embodiments, and for purposes of the present disclosure, the QTc interval is measured using the Bazett formula. Other methods, however, are known in the art, such as the nomogram method, the Frederica formula, or the linear regression equation.

The term "ΔQTc" refers to the difference between a QTc measurement taken prior to intravenous sotalol hydrochloride administration and a QTc measured after intravenous sotalol hydrochloride administration.

The term "PO" stands for "per os" and refers to an oral dosing regimen.

The term "BID" stands for "bis in die" and means twice a day.

The term "subject" refers to a human subject.

An "effective amount" of a drug necessary to achieve a therapeutic effect may vary according to factors such as the age, sex, and weight of the subject. Dosage regimens can be adjusted to provide the optimum therapeutic response.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the subject; slowing in the rate of degeneration or decline; or improving a subject's physical or mental well-being. The treatment or amelioration of symptoms can be based on objective or subject parameters, including the results of a physical examination, neuropsychiatric examinations, or psychiatric evaluation.

Intravenous sotalol was approved by the FDA in 2009. Although FDA guidance requires a slow infusion over five hours coupled with multi-day cardiac monitoring, it has now been surprisingly discovered that it is possible to safely reach a sotalol steady state $C_{max}$ in a subject equal to the sotalol steady state $C_{max}$ typically achieved after BID PO sotalol administration for three days at various sotalol dosage strengths, after about 1 hour of intravenous administration. The ability to reach a steady state $C_{max}$ equal to the steady state $C_{max}$ achieved via oral dosing is surprising because rapid, intravenous sotalol administration was thought to result in high sotalol serum concentration, excessive QT interval prolongation, and on occasion, Torsade de Pointes ventricular tachycardia. See, Somberg, et. al., *Am. J. Ther.* 17(4):365-72 (2010).

Sotalol Initiation Protocol in Naïve Subjects

It has been surprisingly discovered that an about 55 mg to about 64 mg intravenous load of sotalol can be safely delivered over about 1 hour to reach a projected steady state $C_{max}$ of about 800 ng/mL (corresponding to the steady state $C_{max}$ achieved after three days of PO BID dosing of 80 mg sotalol hydrochloride) in sotalol naive subjects. It has likewise been surprisingly discovered that an about 82 mg to about 96 mg intravenous load of sotalol hydrochloride delivered over about 1 hour can safely provide a projected steady state $C_{max}$ of about 1200 ng/mL (corresponding to the steady state $C_{max}$ achieved after three days of PO BID dosing of 120 mg sotalol hydrochloride) in sotalol naïve subjects and that an about 110 mg to about 128 mg intravenous load of sotalol hydrochloride delivered over about 1 hour can safely provide a projected steady state $C_{max}$ of about 1600 ng/mL (corresponding to the steady state $C_{max}$ achieved after three days of PO BID dosing of 160 mg sotalol hydrochloride) in naïve subjects. In each of these cases, intravenous administration of sotalol hydrochloride can be followed at appropriate intervals by oral sotalol hydrochloride to maintain the steady state $C_{max}$ for efficacious treatment or prevention of a given condition.

By administering sotalol according to the dosing protocol described herein, a subject can be discharged from the hospital from about 18 hours to about 24 hours after initiation of intravenous sotalol administration. During the 18-24 hour period, the subject typically experiences at least two sotalol concentration peaks: one following intravenous sotalol hydrochloride administration and one following subsequent oral sotalol hydrochloride administration. In some embodiments, the subject experiences two sotalol concentration peaks over a period of about 15 hours to about 18 hours. In each instance, the subject's peak plasma concentration will approach the steady state $C_{max}$ observed during chronic dosing. As a result, it is possible to assess the QTc interval of a subject corresponding to the full concentration effect of sotalol hydrochloride over an 18-24 hour period and to determine within that period, if the subject can tolerate the dose.

Accordingly, in some embodiments, this disclosure provides a method of safely administering sotalol hydrochloride to a subject in need thereof, the method comprising intravenously administering sotalol hydrochloride over a period of about 60 minutes to reach a sotalol steady state $C_{max}$ in the subject, wherein the subject has a QTc interval during the intravenous administration of sotalol hydrochloride that is less than or equal to 480 msec to 500 msec; and wherein the subject has a ΔQTc during sotalol hydrochloride administration that is less than 20% of the subject's QTc prior to intravenous sotalol administration. In some embodiments, this disclosure provides a method of safely administering sotalol hydrochloride to a subject in need thereof, the method comprising intravenously administering sotalol hydrochloride over a period of about 60 minutes to reach a sotalol steady state $C_{max}$ in the subject, wherein the subject has a QTc interval during the intravenous administration of sotalol hydrochloride that is less than or equal to 480 msec; and wherein the subject has a ΔQTc during sotalol hydrochloride administration that is less than 20% of the subject's QTc prior to intravenous sotalol administration. In other embodiments, this disclosure provides a method of safely administering sotalol hydrochloride to a subject in need thereof, the method comprising intravenously administering sotalol hydrochloride over a period of about 60 minutes to reach a sotalol steady state $C_{max}$ in the subject, wherein the subject has a QTc interval during the intravenous administration of sotalol hydrochloride that is less than or equal to 500 msec; and wherein the subject has a ΔQTc during sotalol hydrochloride administration that is less than 20% of the subject's QTc prior to intravenous sotalol administration.

In some embodiments, about 49.5 to about 70.4 mg of sotalol hydrochloride can be administered intravenously over about 60 minutes to provide an average sotalol steady state $C_{max}$ of about 800 ng/mL. In a particular embodiment, about 55 mg to about 64 mg of sotalol hydrochloride can be administered intravenously over about 60 minutes to provide an average sotalol steady state $C_{max}$ of 800 ng/mL. In some embodiments, about 55 mg to about 64 mg of intravenous sotalol hydrochloride administered over about a 60 minute period can provide a sotalol steady state $C_{max}$ of between about 600 ng/mL and about 1000 ng/mL, between about 600 ng/mL and about 900 ng/mL, between about 600 ng/mL and about 850 ng/mL, between about 600 ng/mL and about 800 ng/mL, between about 600 ng/mL and about 750 ng/mL, between about 600 ng/mL and about 700 ng/mL, between about 700 ng/mL and about 1000 ng/mL, between about 700 ng/mL and about 900 ng/mL, between about 700 ng/mL and about 850 ng/mL, between about 700 ng/mL and about 800 ng/mL, between about 700 ng/mL and about 750 ng/mL, between about 750 ng/mL and about 1000 ng/mL, between about 750 ng/mL and about 900 ng/mL, between about 750 ng/mL and about 850 ng/mL, between about 750 ng/mL and about 800 ng/mL, between about 800 ng/mL and about 1000 ng/mL, between about 800 ng/mL and about 900 ng/mL, between about 800 ng/mL and about 850 ng/mL, between about 850 ng/mL and about 1000 ng/mL, between about 850 ng/mL and about 900 ng/mL, or between about 900 ng/mL and about 1000 ng/mL. In particular embodiments, an about 55 mg to about 64 mg intravenous load of sotalol hydrochloride administered over about 60 minutes can provide a steady state $C_{max}$ of between about 750 ng/mL and about 850 ng/mL.

In some embodiments, between about 0.825 mg/min and about 1.17 mg/min of sotalol hydrochloride can be intravenously administered over the about 60 minute period to achieve the desired steady state $C_{max}$.

In another embodiment, about 73.8 to about 105.6 mg of sotalol hydrochloride can be administered intravenously over about 60 minutes to provide an average sotalol steady state $C_{max}$ of about 1200 ng/mL. In a particular embodiment, about 82 mg to about 96 mg of sotalol hydrochloride can be administered intravenously over about 60 minutes to provide an average sotalol steady state $C_{max}$ of about 1200 ng/mL. In some embodiments, about 82 mg to about 96 mg of intravenous sotalol hydrochloride administered over about 60 minutes can provide a steady state $C_{max}$ of between about 1000 ng/mL and about 1400 ng/mL, between about 1000 ng/mL and about 1300 ng/mL, between about 1000 ng/mL and about 1250 ng/mL, between about 1000 ng/mL and about 1200 ng/mL, between about 1000 ng/mL and about 1150 ng/mL, between about 1000 ng/mL and about 1100 ng/mL, between about 1100 ng/mL and about 1400 ng/mL, between about 1100 ng/mL and about 1300 ng/mL, between about 1100 ng/mL and about 1250 ng/mL, between about 1100 ng/mL and about 1200 ng/mL, between about 1100 ng/mL and about 1150 ng/mL, between about 1150 ng/mL and about 1400 ng/mL, between about 1150 ng/mL and about 1300 ng/mL, between about 1150 ng/mL and about 1250 ng/mL, between about 1150 ng/mL and about 1200 ng/mL, between about 1200 ng/mL and about 1400 ng/mL, between about 1200 ng/mL and about 1300 ng/mL, between about 1200 ng/mL and about 1250 ng/mL, between about 1250 ng/mL and about 1400 ng/mL, between about 1250 ng/mL and about 1300 ng/mL, or between about 1300 ng/mL and about 1400 ng/mL. In particular embodiments, about 82 mg to about 96 mg of sotalol hydrochloride administered intravenously over about 60 minutes can provide a steady state $C_{max}$ of between about 1150 ng/mL and about 1250 ng/mL.

In some embodiments, an intravenous dose of between about 1.23 mg/min and about 1.76 mg/min of sotalol hydrochloride can be administered over a period of about 60 minutes to achieve the desired steady state $C_{max}$.

In yet another embodiment, about 99 to 140.8 mg of sotalol hydrochloride can be administered intravenously over about 60 minutes to provide an average sotalol steady state $C_{max}$ of about 1600 ng/mL. In a particular embodiment, about 110 mg to about 128 mg of sotalol hydrochloride can be administered intravenously over about 60 minutes to provide an average sotalol steady state $C_{max}$ of about 1600 ng/mL. In some embodiments, about 110 mg to about 128 mg of intravenous sotalol hydrochloride administered over a period of about 60 minutes can provide a steady state $C_{max}$ of between about 1400 ng/mL and about 1800 ng/mL, between about 1400 ng/mL and about 1700 ng/mL, between about 1400 ng/mL and about 1650 ng/mL, between about 1400 ng/mL and about 1600 ng/mL, between about 1400 ng/mL and about 1550 ng/mL, between about 1400 ng/mL and about 1500 ng/mL, between about 1500 ng/mL and about 1800 ng/mL, between about 1500 ng/mL and about 1700 ng/mL, between about 1500 ng/mL and about 1650 ng/mL, between about 1500 ng/mL and about 1600 ng/mL, between about 1500 ng/mL and about 1550 ng/mL, between about 1550 ng/mL and about 1800 ng/mL, between about 1550 ng/mL and about 1700 ng/mL, between about 1550 ng/mL and about 1650 ng/mL, between about 1550 ng/mL and about 1600 ng/mL, between about 1600 ng/mL and about 1800 ng/mL, between about 1600 ng/mL and about 1700 ng/mL, between about 1600 ng/mL and about 1650 ng/mL, between about 1650 ng/mL and about 1800 ng/mL, between about 1650 ng/mL and about 1700 ng/mL, or between about 1700 ng/mL and about 1800 ng/mL. In some embodiments, about 110 mg to about 128 mg of sotalol hydrochloride administered intravenously over about 60 minutes can provide a steady state $C_{max}$ of between about 1550 ng/mL and about 1650 ng/mL.

In some embodiments, between about 1.65 mg/min and about 2.35 mg/min of sotalol hydrochloride can be intravenously administered over the about 60 minute period.

Typically, for each of the embodiments described above, the QTc interval of a subject is measured 5 to 15 minutes prior to sotalol initiation and subsequently at 15 minute intervals during intravenous sotalol administration and for about 90 minutes after intravenous administration of sotalol hydrochloride is complete. In other embodiments, the QTc interval of a subject is monitored continuously via telemetry upon intravenous administration of sotalol hydrochloride up to about 90 minutes following complete administration of the drug. It is within the skill of an ordinarily skilled cardiologist to calculate ΔQTc based on these measurements and to increase or decrease sotalol administration appropriately.

In some embodiments, where a subject has been initiated on about 55 mg to about 64 mg of intravenous sotalol over about a 60 minute period, 80 mg of sotalol hydrochloride can be administered orally between about 1 hour and about 6 hours after the completion of the intravenous administration of the about 55 mg to about 64 mg of sotalol hydrochloride. In some embodiments, 80 mg of sotalol hydrochloride can be administered orally between about 1 hour and about 6 hours, between about 2 hours and about 5 hours, between about 2 hours and about 4 hours, between about 2 hours and about 3 hours, between about 3 hours and about 6 hours, between about 3 hours and about 5 hours, between about 3 hours and about 4 hours, between about 4 hours and about 6 hours, between about 4 hours and about 5 hours, or between about 5 hours and about 6 hours after the completion of the intravenous administration of about 55 mg to about 64 mg of sotalol hydrochloride.

In some embodiments, between about 2 hours and 5 hours after oral administration of 80 mg of sotalol hydrochloride, further oral administration is discontinued or reduced when the subject has a QTc interval that is greater than 480 msec to 500 msec; or when the subject has a ΔQTc that is greater than or equal to 20% of the subject's QTc prior to sotalol administration. In some embodiments, between about 2 hours and 5 hours after oral administration of 80 mg of sotalol hydrochloride, further oral administration is discontinued or reduced when the subject has a QTc interval that is greater than 480 msec; or when the subject has a ΔQTc that is greater than or equal to 20% of the subject's QTc prior to sotalol administration. In other embodiments, between about 2 hours and 5 hours after oral administration of 80 mg of sotalol hydrochloride, further oral administration is discontinued or reduced when the subject has a QTc interval that is greater than 500 msec; or when the subject has a ΔQTc that is greater than or equal to 20% of the subject's QTc prior to sotalol administration.

Alternatively, and in another embodiment, a BID regimen of PO 80 mg sotalol hydrochloride can be initiated when the subject has a QTc interval at between about 2 hours and about 3 hours after the initial oral administration of sotalol hydrochloride that is less than or equal to 480 msec to 500 msec; or when the subject has a ΔQTc that is less than 20% of the subject's QTc prior to sotalol administration. In some embodiments, a BID regimen of PO 80 mg sotalol hydrochloride can be initiated when the subject has a QTc interval at between about 2 hours and about 3 hours after the initial oral administration of sotalol hydrochloride that is less than or equal to 480 msec; or when the subject has a ΔQTc that is less than 20% of the subject's QTc prior to sotalol administration. In other embodiments, a BID regimen of PO 80 mg sotalol hydrochloride can be initiated when the subject has a QTc interval at between about 2 hours and about 3 hours after the initial oral administration of sotalol hydrochloride that is less than or equal to 500 msec; or when the subject has a ΔQTc that is less than 20% of the subject's QTc prior to sotalol administration.

In another embodiment, such when the subject exhibits impaired renal function, i.e. a glomerular filtration rate (GFR) of between about 45-60 mL/min, the maintenance dose of oral sotalol can be administered over a longer dosing interval. For example, a once daily regimen of 80 mg PO sotalol hydrochloride can be initiated when the subject has a QTc interval at between about 2 hours and about 3 hours after initial oral administration of 80 mg of sotalol hydrochloride that is less than or equal to 500 msec; or when the subject has a ΔQTc that is less than 20% of the subject's QTc prior to sotalol administration.

In some embodiments, where a subject has been initiated on about 82 mg to about 96 mg of intravenous sotalol over about a 60 minute period, 120 mg of sotalol hydrochloride can be administered orally between about 1 hour and about 6 hours after completion of the intravenous administration of the about 82 mg to about 96 mg of sotalol hydrochloride. In some embodiments, 120 mg of sotalol hydrochloride is administered orally between about 2 hours and about 6 hours, between about 2 hours and about 5 hours, between about 2 hours and about 4 hours, between about 2 hours and about 3 hours, between about 3 hours and about 6 hours, between about 3 hours and about 5 hours, between about 3 hours and about 4 hours, between about 4 hours and about 6 hours, between about 4 hours and about 5 hours, or between about 5 hours and about 6 hours after completion of the intravenous administration of about 82 mg to about 96 mg of sotalol hydrochloride.

In some embodiments, between about 2 hours and 5 hours after oral administration of 120 mg of sotalol hydrochloride, further oral administration is discontinued or reduced when the subject has a QTc interval that is greater than 480 to 500 msec; or when the subject has a ΔQTc that is greater than or equal to 20% of the subject's QTc prior to initial oral administration of sotalol hydrochloride. In a particular embodiment, between about 2 hours and 5 hours after oral administration of 120 mg of sotalol hydrochloride, further oral administration is discontinued or reduced when the subject has a QTc interval that is greater than 480 msec; or when the subject has a ΔQTc that is greater than or equal to 20% of the subject's QTc prior to initial oral administration of sotalol hydrochloride. In another embodiment, between about 2 hours and 5 hours after oral administration of 120 mg of sotalol hydrochloride, further oral administration is discontinued or reduced when the subject has a QTc interval that is greater than 500 msec; or when the subject has a ΔQTc that is greater than or equal to 20% of the subject's QTc prior to initial oral administration of sotalol hydrochloride.

Alternatively, and in another embodiment, a BID regimen of PO 120 mg sotalol hydrochloride can be initiated when the subject has a QTc interval at between about 2 hours and about 3 hours after initial oral administration of sotalol hydrochloride that is less than or equal to 500 msec; or when the subject has a ΔQTc that is less than 20% of the subject's QTc prior to sotalol administration. In a particular embodiment, a BID regimen of PO 120 mg sotalol hydrochloride can be initiated when the subject has a QTc interval at between about 2 hours and about 3 hours after initial oral administration of sotalol hydrochloride that is less than or equal to 480 msec; or when the subject has a ΔQTc that is less than 20% of the subject's QTc prior to sotalol administration. In another embodiment, a BID regimen of PO 120 mg sotalol hydrochloride can be initiated when the subject has a QTc interval at between about 2 hours and about 3 hours after initial oral administration of sotalol hydrochloride that is less than or equal to 500 msec; or when the subject has a ΔQTc that is less than 20% of the subject's QTc prior to sotalol administration.

In another embodiment, such when the subject exhibits impaired renal function, i.e. a glomerular filtration rate (GFR) of between about 45-60 mL/min, the maintenance dose of oral sotalol can be administered over a longer dosing interval. For example, a once daily regimen of 120 mg PO sotalol hydrochloride can be initiated when the subject has a QTc interval at between about 2 hours and about 3 hours after initial oral administration of 120 mg of sotalol hydrochloride that is less than or equal to 500 msec; or when the subject has a ΔQTc that is less than 20% of the subject's QTc prior to sotalol administration.

In some embodiments, where a subject has been initiated on about 110 mg to about 128 mg of intravenous sotalol over about a 60 minute period, 160 mg of sotalol hydrochloride can be administered orally between about 1 hour and about 6 hours after completion of the intravenous administration of about 110 mg to about 128 mg of sotalol hydrochloride. In some embodiments, 160 mg of sotalol hydrochloride can be administered orally between about 2 hours and about 6 hours, between about 2 and about 5 hours, between about 2 and about 4 hours, between about 2 hours and about 3 hours, between about 3 hours and about 6 hours, between about 3 hours and about 5 hours, between about 3 hours and about 4 hours, between about 4 hours and about 6 hours, between about 4 hours and about 5 hours, or between about 5 hours and about 6 hours after completion of the intravenous administration of about 110 mg to about 128 mg of sotalol hydrochloride.

In some embodiments, between about 2 hours and 5 hours after initial oral administration of 160 mg of sotalol hydrochloride, further oral administration can be discontinued or reduced when the subject has a QTc interval that is greater than 480 to 500 msec; or when the subject has a ΔQTc that is greater than or equal to 20% of the subject's QTc prior to sotalol administration. In one embodiment, between about 2 hours and 5 hours after initial oral administration of 160 mg of sotalol hydrochloride, further oral administration can be discontinued or reduced when the subject has a QTc interval that is greater than 480 msec; or when the subject has a ΔQTc that is greater than or equal to 20% of the subject's QTc prior to sotalol administration. In another embodiment, between about 2 hours and 5 hours after initial oral administration of 160 mg of sotalol hydrochloride, further oral administration can be discontinued or reduced when the subject has a QTc interval that is greater than 500 msec; or when the subject has a ΔQTc that is greater than or equal to 20% of the subject's QTc prior to sotalol administration.

Alternatively, and in another embodiment, a BID regimen of PO of 160 mg of sotalol hydrochloride can be initiated when the subject has a QTc interval at between about 2 hours and about 3 hours after initial oral administration of sotalol hydrochloride that is less than or equal to 480 to 500 msec; or when the subject has a ΔQTc that is less than 20% of the subject's QTc prior to sotalol administration. In a particular embodiment, a BID regimen of PO of 160 mg of sotalol hydrochloride can be initiated when the subject has a QTc interval at between about 2 hours and about 3 hours after initial oral administration of sotalol hydrochloride that is less than or equal to 480 msec; or when the subject has a ΔQTc that is less than 20% of the subject's QTc prior to sotalol administration. In another embodiment, a BID regimen of PO of 160 mg of sotalol hydrochloride can be initiated when the subject has a QTc interval at between about 2 hours and about 3 hours after initial oral administration of sotalol hydrochloride that is less than or equal to 500 msec; or when the subject has a ΔQTc that is less than 20% of the subject's QTc prior to sotalol administration.

In another embodiment, such when the subject exhibits impaired renal function, i.e. a glomerular filtration rate (GFR) of between about 45-60 mL/min, the maintenance dose of oral sotalol can be administered over a longer dosing interval. For example, a once daily regimen of 160 mg PO sotalol hydrochloride can be initiated when the subject has a QTc interval at between about 2 hours and about 3 hours after initial oral administration of 160 mg of sotalol hydrochloride that is less than or equal to 500 msec; or when the subject has a ΔQTc that is less than 20% of the subject's QTc prior to sotalol administration.

Dose Escalation Protocol

The method of rapid sotalol introduction described herein can also be applied to dose escalation, for example when a subject needs to transition from 80 mg BID PO to 120 mg BID PO; or from 120 mg BID PO to 160 mg BID PO.

For example, subjects receiving 80 or 120 mg BID PO sotalol hydrochloride can be safely transitioned to 120 or 160 mg BID PO sotalol hydrochloride, respectively, via the administration of an intravenous infusion about 12 hours after the last oral dose of sotalol hydrochloride, i.e. when the concentration of sotalol hydrochloride is at a trough (steady state $C_{min}$).

Dose Escalation to from 80 mg to 120 mg Oral Sotalol Hydrochloride

In some embodiments, about 49.5 to about 70.4 mg of sotalol hydrochloride can be administered intravenously over about 60 minutes to provide an average sotalol steady state $C_{ma}$, of about 1200 ng/mL. In a particular embodiment, about 55 mg to about 64 mg of sotalol hydrochloride can be safely administered intravenously over a period of about 60 minutes to provide an average sotalol steady state $C_{max}$ of about 1200 ng/mL (corresponding to the steady state $C_{max}$ achieved after three days of PO BID dosing of 120 mg sotalol hydrochloride) in a subject dosed with 80 mg of oral sotalol hydrochloride between about 12 hours and about 24 hours before the intravenous administration. In some embodiments, the sotalol hydrochloride can be administered to the subject at a rate between about 0.825 mg/min and about 1.17 mg/min over a period of about 60 minutes.

In some embodiments, during administration of between about 0.825 mg/min and about 1.17 mg/min of sotalol hydrochloride over a period of about 60 minutes, intravenous administration is discontinued or reduced when the subject has a QTc interval that is greater than 480 to 500 msec; or when the subject has a ΔQTc that is greater than or equal to 20% of the subject's QTc prior to sotalol administration. In a particular embodiment, during administration of between about 0.825 mg/min and about 1.17 mg/min of sotalol hydrochloride over a period of about 60 minutes, intravenous administration is discontinued or reduced when the subject has a QTc interval that is greater than 480 msec; or when the subject has a ΔQTc that is greater than or equal to 20% of the subject's QTc prior to sotalol administration. In another embodiment, during administration of between about 0.825 mg/min and about 1.17 mg/min of sotalol hydrochloride over a period of about 60 minutes, intravenous administration is discontinued or reduced when the subject has a QTc interval that is greater than 500 msec; or when the subject has a ΔQTc that is greater than or equal to 20% of the subject's QTc prior to sotalol administration.

Alternatively, and in other embodiments, 120 mg of sotalol hydrochloride can be administered orally between about 1 hour and about 6 hours after the completion of the intravenous administration of about 55 mg to about 64 mg of sotalol hydrochloride. In some embodiments, 120 mg of sotalol hydrochloride is administered orally between about 1 hour and about 6 hours, between about 2 and about 5 hours, between about 2 and about 4 hours, between about 2 hours and about 3 hours, between about 3 hours and about 6 hours, between about 3 hours and about 5 hours, between about 3 hours and about 4 hours, between about 4 hours and about 6 hours, between about 4 hours and about 5 hours, or between about 5 hours and about 6 hours after the completion of the intravenous administration of about 55 mg to about 64 mg of sotalol hydrochloride.

In some embodiments, oral administration is discontinued or reduced when the subject has a QTc interval that is greater than 480 msec to 500 msec; or when the subject has a ΔQTc that is greater than or equal to 20% of the subject's QTc prior to the oral administration of sotalol hydrochloride. In a particular embodiment, oral administration is discontinued or reduced when the subject has a QTc interval that is greater than 480 msec; or when the subject has a ΔQTc that is greater than or equal to 20% of the subject's QTc prior to the oral administration of sotalol hydrochloride. In another embodiment, oral administration is discontinued or reduced when the subject has a QTc interval that is greater than 500 msec; or when the subject has a ΔQTc that is greater than or equal to 20% of the subject's QTc prior to the oral administration of sotalol hydrochloride.

In other embodiments, BID PO administration of 120 mg of sotalol hydrochloride can be initiated when the subject has a QTc interval at between about 2 hours and about 3 hours after oral administration of 120 mg of sotalol hydrochloride that is less than or equal to 480 msec to 500 msec; or when the subject has a ΔQTc that is less than 20% of the subject's QTc prior to sotalol administration. In a particular embodiment, BID PO administration of 120 mg of sotalol hydrochloride can be initiated when the subject has a QTc interval at between about 2 hours and about 3 hours after oral administration of 120 mg of sotalol hydrochloride that is less than or equal to 480 msec; or when the subject has a ΔQTc that is less than 20% of the subject's QTc prior to sotalol administration. In another embodiment, BID PO administration of 120 mg of sotalol hydrochloride can be initiated when the subject has a QTc interval at between about 2 hours and about 3 hours after oral administration of 120 mg of sotalol hydrochloride that is less than or equal to 500 msec; or when the subject has a ΔQTc that is less than 20% of the subject's QTc prior to sotalol administration.

Subjects with impaired renal function safely transitioned to the higher dose can take 120 mg sotalol once daily as discussed elsewhere herein.

Dose Escalation from 120 mg to 160 mg Oral Sotalol Hydrochloride

In some embodiments, about 63 to about 88 mg of sotalol hydrochloride can be administered intravenously over about 60 minutes to provide an average sotalol steady state $C_{max}$ of about 1600 ng/mL. In a particular embodiment, about 70 mg to about 80 mg of sotalol hydrochloride can be safely administered intravenously over a period of about 60 minutes to provide an average sotalol steady state $C_{max}$ of about 1600 ng/mL (corresponding to the steady state $C_{max}$ achieved after three days of PO BID dosing of 160 mg sotalol hydrochloride) in a subject dosed with 120 mg of oral sotalol hydrochloride between about 12 hours and about 24 hours before the intravenous administration. In some embodiments, the sotalol hydrochloride can be administered to the subject at a rate between about 1.05 mg/min and about 1.47 mg/min over a period of about 60 minutes.

In some embodiments, during administration of between about 1.05 mg/min and about 1.47 mg/min of sotalol hydrochloride over a period of about 60 minutes, intravenous administration is discontinued or reduced when the subject has a QTc interval that is greater than 480 to 500 msec; or when the subject has a ΔQTc that is greater than or equal to 20% of the subject's QTc prior to sotalol administration. In one embodiment, during administration of between about 1.05 mg/min and about 1.47 mg/min of sotalol hydrochloride over a period of about 60 minutes, intravenous administration is discontinued or reduced when the subject has a QTc interval that is greater than 480 msec; or when the subject has a ΔQTc that is greater than or equal to 20% of the subject's QTc prior to sotalol administration. In another embodiment, during administration of between about 1.05 mg/min and about 1.47 mg/min of sotalol hydrochloride over a period of about 60 minutes, intravenous administration is discontinued or reduced when the subject has a QTc interval that is greater than 500 msec; or when the subject has a ΔQTc that is greater than or equal to 20% of the subject's QTc prior to sotalol administration.

Alternatively, and in other embodiments, 160 mg of sotalol hydrochloride can be administered orally between about 1 hour and about 6 hours after the completion of the intravenous administration of about 70 mg to about 80 mg of sotalol hydrochloride. In some embodiments, 160 mg of sotalol hydrochloride can be administered orally between about 1 hour and about 6 hours, between about 2 hours and about 5 hours, between about 2 hours and about 4 hours, between about 2 hours and about 3 hours, between about 3 hours and about 6 hours, between about 3 hours and about 5 hours, between about 3 hours and about 4 hours, between about 4 hours and about 6 hours, between about 4 hours and about 5 hours, or between about 5 hours and about 6 hours after the completion of the intravenous administration of about 70 mg to about 80 mg of sotalol hydrochloride.

In some embodiments, further oral administration is discontinued or reduced when the subject has a QTc interval that is greater than 480 msec to 500 msec; or when the subject has a ΔQTc that is greater than or equal to 20% of the subject's QTc prior to sotalol administration. In one embodiment, further oral administration is discontinued or reduced when the subject has a QTc interval that is greater than 480 msec; or when the subject has a ΔQTc that is greater than or equal to 20% of the subject's QTc prior to sotalol administration. In another embodiment, further oral administration is discontinued or reduced when the subject has a QTc interval that is greater than 500 msec; or when the subject has a ΔQTc that is greater than or equal to 20% of the subject's QTc prior to sotalol administration.

In other embodiments, BID PO administration of 160 mg of sotalol hydrochloride can be initiated when the subject has a QTc interval at between about 2 hours and about 3 hours after initial oral administration of sotalol hydrochloride that is less than or equal to 480 msec to 500 msec; or when the subject has a ΔQTc that is less than 20% of the subject's QTc prior to sotalol administration. In some embodiments, BID PO administration of 160 mg of sotalol hydrochloride can be initiated when the subject has a QTc interval at between about 2 hours and about 3 hours after initial oral administration of sotalol hydrochloride that is less than or equal to 480 msec; or when the subject has a ΔQTc that is less than 20% of the subject's QTc prior to sotalol administration. In other embodiments, BID PO administration of 160 mg of sotalol hydrochloride can be initiated when the subject has a QTc interval at between about 2 hours and about 3 hours after initial oral administration of sotalol hydrochloride that is less than or equal to 500 msec; or when the subject has a ΔQTc that is less than 20% of the subject's QTc prior to sotalol administration.

Subjects with impaired renal function safely transitioned to the higher dose can take 160 mg sotalol once daily as discussed elsewhere herein.

Method of Reducing Hospital Stay

In some embodiments, the disclosure provides a method of reducing a hospital stay in a subject in need of treatment or prevention of atrial fibrillation, atrial flutter, or a combination thereof, the method comprising introducing a subject to sotalol hydrochloride administered intravenously over a period of about 60 minutes in the absence of further sotalol administration for a period of about 1 hour to about 6 hours after the period of about 60 minutes.

In some embodiments, about 0.825 mg/min to about 1.17 mg/min of sotalol hydrochloride is intravenously administered over the about 60 minute period. In some embodiments, the intravenous administration of sotalol hydrochloride results in a sotalol steady state $C_{max}$ of between about 750 ng/mL and about 850 ng/mL in the subject.

In some embodiments, about 1.23 mg/min to about 1.76 mg/min of sotalol hydrochloride is intravenously administered over the about 60 minute period. In some embodiments, the intravenous administration of sotalol hydrochloride results in a sotalol steady state $C_{max}$ of between about 1150 ng/mL and about 1250 ng/mL in the subject.

In some embodiments, about 1.65 mg/min to about 2.35 mg/min of sotalol hydrochloride is intravenously administered over the about 60 minute period. In some embodiments, the intravenous administration of sotalol hydrochloride results in a sotalol steady state $C_{max}$ of between about 1550 ng/mL and about 1650 ng/mL in the subject.

In some embodiments, where the subject received 80 mg oral sotalol hydrochloride about 12 hours to about 24 hours before the intravenous administration, about 0.825 mg/min to about 1.17 mg/min of sotalol hydrochloride can be intravenously administered over the about 60 minute period to safely escalate sotalol hydrochloride dosing to 120 mg oral sotalol hydrochloride.

In yet another embodiment, where the subject received 120 mg oral sotalol hydrochloride about 12 hours to about 24 hours before the intravenous administration, between about 1.05 mg/min and about 1.47 mg/min of sotalol hydrochloride can be intravenously administered over the about 60 minute period to safely escalate sotalol hydrochloride dosing to 160 mg oral sotalol hydrochloride.

In any of the embodiments described above, the intravenous administration of sotalol hydrochloride can be discontinued or reduced when the subject has a QTc interval after intravenous sotalol hydrochloride initiation that is greater than 480 msec to 500 msec; or wherein the subject has a ΔQTc that is greater than or equal to 20% of the subject's QTc prior to sotalol administration. In any of the embodiments described above, the intravenous administration of sotalol hydrochloride can be discontinued or reduced when the subject has a QTc interval after intravenous sotalol hydrochloride initiation that is greater than 480 msec; or wherein the subject has a ΔQTc that is greater than or equal to 20% of the subject's QTc prior to sotalol administration. Alternatively, in any of the embodiments described above, the intravenous administration of sotalol hydrochloride can be discontinued or reduced when the subject has a QTc interval after intravenous sotalol hydrochloride initiation that is greater than 500 msec; or wherein the subject has a ΔQTc that is greater than or equal to 20% of the subject's QTc prior to sotalol administration.

In some embodiments, sotalol hydrochloride is orally administered between about 1 hour and about 6 hours after completion of the intravenous administration.

In some embodiments, 80 mg of sotalol hydrochloride can be orally administered between about 1 and about 6 hours after completing intravenous administration of about 0.825 mg/min to about 1.17 mg/min of sotalol hydrochloride.

In some embodiments, 120 mg of sotalol hydrochloride can be orally administered between about 1 hour and about 6 hours after completing intravenous administration of about 1.23 mg/min to about 1.76 mg/min of sotalol hydrochloride.

In some embodiments, 160 mg of sotalol hydrochloride can be orally administered between about 1 hour and about 6 hours after completing intravenous administration of about 1.65 mg/min to about 2.35 mg/min of sotalol hydrochloride.

In some embodiments, the oral administration of sotalol hydrochloride is discontinued or reduced when the subject has a QTc interval at between about 2 hours and about 3 hours after oral administration of sotalol hydrochloride that is greater than 500 msec; or wherein the subject has a ΔQTc that is greater than or equal to 20% of the subject's QTc prior to intravenous sotalol administration. In a particular embodiment, the oral administration of sotalol hydrochloride is discontinued or reduced when the subject has a QTc interval at between about 2 hours and about 3 hours after oral administration of sotalol hydrochloride that is greater than 480 msec; or wherein the subject has a ΔQTc that is greater than or equal to 20% of the subject's QTc prior to intravenous sotalol administration. In another particular embodiment, the oral administration of sotalol hydrochloride is discontinued or reduced when the subject has a QTc interval at between about 2 hours and about 3 hours after oral administration of sotalol hydrochloride that is greater than 500 msec; or wherein the subject has a ΔQTc that is greater than or equal to 20% of the subject's QTc prior to intravenous sotalol administration.

As described elsewhere herein, when a subject has a QTc interval that is acceptable and/or wherein the subject has a ΔQTc that is less than or equal to 20% of the subject's QTc prior to intravenous sotalol administration, the subject can be transitioned to BID PO dosing, or QD (once daily) PO dosing, as appropriate for the subject's renal function.

EMBODIMENTS

In addition to the various embodiments described above, the present disclosure includes the following specific embodiments numbered E1 through E27. This list of embodiments is presented as an exemplary list and the application is not limited to these embodiments.

E1. A method of treating or preventing atrial fibrillation, atrial flutter, or a combination thereof in a subject in need thereof, the method comprising intravenously administering to the subject between about 0.825 mg/min and about 1.17 mg/min of sotalol hydrochloride over a period of about 60 minutes.

E2. The method of E1, further comprising discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

E3. The method of E1, wherein the intravenous administration of sotalol hydrochloride results in a sotalol steady state $C_{max}$ of between about 750 ng/mL and about 850 ng/mL in the subject.

E4. The method of E3, further comprising orally administering to the subject 80 mg of sotalol hydrochloride between about 1 hour and about 6 hours after completion of the intravenous administration.

E5. The method of E4, further comprising discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

E6. The method of E4, further comprising initiating an oral BID administration regimen of sotalol hydrochloride when the subject has a QTc interval at between about 2 hours and about 3 hours after oral administration of sotalol hydrochloride that is less than or equal to 500 msec; or wherein the subject has a ΔQTc that is less than 20% of the subject's QTc prior to intravenous sotalol administration.

E7. A method of treating or preventing atrial fibrillation, atrial flutter, or a combination thereof in a subject in need thereof, the method comprising intravenously administering to the subject between about 1.23 mg/min and about 1.76 mg/min of sotalol hydrochloride over a period of about 60 minutes.

E8. The method of E7, further comprising discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

E9. The method of E7, wherein the intravenous administration of sotalol hydrochloride results in a sotalol steady state $C_{max}$ of between about 1150 ng/mL and about 1250 ng/mL in the subject.

E10. The method of E9, further comprising orally administering to the subject 120 mg of sotalol hydrochloride between about 1 hour and about 6 hours after completion of the intravenous administration.

E11. The method of E10, further comprising discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

E12. The method of E10, further comprising initiating an oral BID administration regimen of sotalol hydrochloride when the subject has a QTc interval at between about 2 hours and about 3 hours after oral administration of sotalol hydrochloride that is less than or equal to 500 msec; or wherein the subject has a ΔQTc that is less than 20% of the subject's QTc prior to intravenous sotalol administration.

E13. A method of treating atrial fibrillation, atrial flutter, or a combination thereof in a subject in need thereof, the method comprising intravenously administering to the subject between about 1.65 mg/min and about 2.35 mg/min of sotalol hydrochloride over a period of about 60 minutes.

E14. The method of E13, further comprising discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

E15. The method of E13, wherein the intravenous administration of sotalol hydrochloride results in a sotalol steady state $C_{max}$ of between about 1550 ng/mL and about 1650 ng/mL in the subject.

E16. The method of E15, further comprising orally administering to the subject 160 mg of sotalol hydrochloride between about 1 hour and about 6 hours after completion of the intravenous administration.

E17. The method of E16, further comprising discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

E18. The method of E16, further comprising initiating an oral BID administration regimen of sotalol hydrochloride when the subject has a QTc interval at between about 2 hours and 3 hours after oral administration of sotalol hydrochloride that is less than or equal to 500 msec; or wherein the subject has a ΔQTc that is less than 20% the subject's QTc prior to intravenous sotalol administration.

E19. A method of treating or preventing atrial fibrillation, atrial flutter, or a combination thereof in a subject in need thereof, the method comprising intravenously administering to the subject between about 0.825 mg/min and about 1.17 mg/min of sotalol hydrochloride over a period of about 60 minutes, wherein the subject received an administration of sotalol hydrochloride between about 12 hours and about 24 hours before the intravenous administration.

E20. The method of E19, wherein the subject received an oral administration of 80 mg of oral sotalol hydrochloride between about 12 and about 24 hours before the intravenous administration.

E21. The method of E19, further comprising discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

E22. The method of E19, wherein the intravenous administration of sotalol hydrochloride results in a sotalol steady state $C_{max}$ of between about 1150 ng/mL and about 1250 ng/mL in the subject.

E23. The method of E22, further comprising orally administering to the subject 120 mg of sotalol hydrochloride between about 1 hour and about 6 hours after completion of the intravenous administration.

E24. The method of E23, further comprising discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

E25. The method of E23, further comprising initiating an oral BID administration regimen of sotalol hydrochloride when the subject has a QTc interval at between about 2 hours and 3 hours after oral administration of sotalol hydrochloride that is less than or equal to 500 msec; or wherein the subject has a ΔQTc that is less than 20% the subject's QTc prior to intravenous sotalol administration.

E26. A method of treating or preventing atrial fibrillation, atrial flutter, or a combination thereof in a subject in need thereof, the method comprising intravenously administering to the subject between about 1.05 mg/min and about 1.47 mg/min of sotalol hydrochloride over a period of about 60 minutes, wherein the subject received an administration of sotalol hydrochloride between about 12 hours and about 24 hours before the intravenous administration.

E27. The method of E26, wherein the subject received an oral administration of 120 mg of oral sotalol hydrochloride between about 12 and about 24 hours before the intravenous administration.

E28. The method of E26, further comprising discontinuing or reducing intravenous administration of sotalol hydrochloride when the subject has a QTc interval after intravenous sotalol hydrochloride initiation that is greater than 500 msec; or wherein the subject has a ΔQTc that is greater than or equal to 20% of the subject's QTc prior to sotalol administration.

E29. The method of E26, wherein the intravenous administration of sotalol hydrochloride results in a sotalol steady state $C_{max}$ of between about 1550 ng/mL and about 1650 ng/mL in the subject.

E30. The method of E29, further comprising orally administering to the subject 160 mg of sotalol hydrochloride between about 1 hour and about 6 hours after completion of the intravenous administration.

E31. The method of E30, further comprising discontinuing or reducing oral administration of sotalol hydrochloride when the subject has a QTc interval at between about 2 hours and about 5 hours after oral administration of sotalol hydrochloride that is greater than 500 msec; or wherein the subject has a ΔQTc that is greater than or equal to 20% of the subject's QTc prior to intravenous sotalol administration.

E32. The method of E30, further comprising initiating an oral BID administration regimen of sotalol hydrochloride when the subject has a QTc interval at between about 2 hours and 3 hours after oral administration of sotalol hydrochloride that is less than or equal to 500 msec; or wherein the subject has a ΔQTc that is less than 20% the subject's QTc prior to intravenous sotalol administration.

E33. A method of reducing a hospital stay of a subject in need of treatment or prevention of atrial fibrillation, atrial flutter, or a combination thereof, the method comprising stabilizing a subject on sotalol hydrochloride administered intravenously over a period of about 60 minutes in the absence of further sotalol administration for a period of about 1 hour to about 6 hours after the period of about 60 minutes.

E34. The method of E33, wherein the hospital stay is reduced to between about 18 hours and about 24 hours.

E35. The method of E33, wherein the hospital stay is reduced to between about 20 hours and about 24 hours.

E36. The method of E33, wherein between about 0.825 mg/min and about 1.17 mg/min of sotalol hydrochloride is intravenously administered over the about 60 minute period.

E37. The method of E33, wherein between about 1.23 mg/min and about 1.76 mg/min of sotalol hydrochloride is intravenously administered over the about 60 minute period.

E38. The method of E33, wherein between about 1.65 mg/min and about 2.35 mg/min of sotalol hydrochloride is intravenously administered over the about 60 minute period.

E39. The method of E33, wherein the subject received oral sotalol hydrochloride between about 12 hours and about 24 hours before the intravenous administration.

E40. The method of E39, wherein between about 0.825 mg/min about 1.17 mg/min of sotalol hydrochloride is intravenously administered over the about 60 minute period.

E41. The method of E39, wherein between about 1.05 mg/min and about 1.47 mg/min of sotalol hydrochloride is intravenously administered over the about 60 minute period.

E42. The method of E33, wherein the intravenous administration of sotalol hydrochloride is discontinued or reduced when the subject has a QTc interval after intravenous sotalol hydrochloride initiation that is greater than 500 msec; or wherein the subject has a ΔQTc that is greater than or equal to 20% of the subject's QTc prior to sotalol administration.

E43. The method of E36, wherein the intravenous administration of sotalol hydrochloride results in a sotalol steady state $C_{max}$ of between about 750 ng/mL and about 850 ng/mL in the subject.

E44. The method of E37, wherein the intravenous administration of sotalol hydrochloride results in a sotalol steady state $C_{max}$ of between about 1150 ng/mL and about 1250 ng/mL in the subject.

E45. The method of E38, wherein the intravenous administration of sotalol hydrochloride results in a sotalol steady state $C_{max}$ of between about 1550 ng/mL and about 1650 ng/mL in the subject.

E46. The method E33, further comprising orally administering to the subject sotalol hydrochloride between about 1 hour and about 6 hours after completion of the intravenous administration.

E47. The method of E33, wherein 80 mg of sotalol hydrochloride is orally administered between about 5 and about 8 hours after completion of intravenous administration of between about 0.825 mg/min and about 1.17 mg/min of sotalol hydrochloride.

E48. The method of E33, wherein 120 mg of sotalol hydrochloride is orally administered between about 1 hour and about 6 hours after completion of intravenous administration of between about 1.23 mg/min and about 1.76 mg/min of sotalol hydrochloride.

E49. The method of E33, wherein 160 mg of sotalol hydrochloride is orally administered between about 1 hour and about 6 hours after completion of intravenous administration of between about 1.65 mg/min and about 2.35 mg/min of sotalol hydrochloride.

E50. The method of E46, wherein the oral administration of sotalol hydrochloride is discontinued or reduced when the subject has a QTc interval at between about 2 hours and about 3 hours after oral administration of sotalol hydrochloride that is greater than 500 msec; or wherein the subject has a ΔQTc that is greater than or equal to 20% of the subject's QTc prior to intravenous sotalol administration.

E51. The method of E46, wherein an oral administration BID regimen of sotalol hydrochloride is initiated when the subject has a QTc interval at between about 2 hours and about 3 hours after oral administration of sotalol hydrochloride that is less than or equal to 500 msec; or wherein the subject has a ΔQTc that is less than 20% of the subject's QTc prior to intravenous sotalol administration.

E52. A method of administering sotalol hydrochloride to a subject in need thereof, the method comprising intravenously administering sotalol hydrochloride over a period of about 60 minutes to reach a sotalol steady state $C_{max}$ in the subject, wherein the subject has a QTc interval during the intravenous administration of sotalol hydrochloride that is less than or equal to 500 msec; and wherein the subject has a ΔQTc during sotalol hydrochloride administration that is less than 20% of the subject's QTc prior to intravenous sotalol administration.

E53. The method of E52, wherein the sotalol steady state $C_{max}$ is between about 750 ng/mL and about 850 ng/mL.

E54. The method of E52, wherein the steady sotalol state $C_{max}$ is between about 1150 ng/mL and about 1250 ng/mL.

E55. The method of E52, wherein the steady sotalol state $C_{max}$ is between about 1550 ng/mL and about 1650 ng/mL.

E56. The method of E52, wherein between about 0.825 mg/min and about 1.17 mg/min of sotalol hydrochloride is intravenously administered over the about 60 minute period.

E57. The method of E52, wherein between about 1.23 mg/min and about 1.76 mg/min of sotalol hydrochloride is intravenously administered over the about 60 minute period.

E58. The method of E52, wherein between about 1.65 mg/min and about 2.35 mg/min of sotalol hydrochloride is intravenously administered over the about 60 minute period.

E59. A method to administer a loading dose of Sotalol entirely intravenously to a target maximum serum concentration that a subject is expected to be exposed in the course of chronic oral dosing of Sotalol.

E60. A method to administer sotalol intravenously to a target concentration in order to see the maximum QTc interval increment that can be expected to be expressed by a subject in the course of chronic oral therapy, while maximizing subject safety during initial loading process.

E61. A method permitting the targeting of the projected maximum concentration of sotalol hydrochloride that may be attained on chronic dosing in a period of one hour, permitting the adjustment of the dosing, or its cessation for subject safety dependent on QTc interval prolongation.

E62. A way to initiate sotalol hydrochloride therapy in a subject with an indication to receive chronic sotalol therapy employing an intravenous infusion.

E63. The use of an intravenous infusion to obtain sotalol hydrochloride steady state $C_{max}$ concentration to the level obtained with chronic oral sotalol hydrochloride dosing.

E64. A way to obtain steady state $C_{max}$ to observe changes in cardiac repolarization such that the increase in QTc is not greater than specified in guidelines and thus, not risking the development of life threatening ventricular arrhythmias.

E65. A method of administering sotalol hydrochloride, observing the changes in QTc such that if the QTc increases beyond acceptable parameters, the infusion can be terminated immediately, enhancing subject safety.

E66. A method of increasing sotalol hydrochloride dose from low dose oral therapy to higher dose oral therapy using an intravenous infusion.

E67. A method of dose escalation of sotalol hydrochloride such that the infusion obtains the projected steady state $C_{max}$ and thus maximum QTc changes in a brief period of time, avoiding changes in QTc in excess of those expected to be experienced by a subject receiving an appropriate dose of sotalol and thus reducing the risk of drug induced arrhythmias.

E68. A method of dose initiation and dose escalation employing intravenous sotalol hydrochloride in subjects with renal dysfunction. Providing the attainment of steady state $C_{max}$ and thus, the full exposure of QTc changes under electrocardiographic observation within 24 hours of exposure.

EXAMPLES

The following examples are illustrative and non-limiting, of the methods described herein. Suitable modifications and adaptations of the variety of conditions, formulations, and other parameters normally encountered in the field and which are obvious to those skilled in the art in view of this disclosure are within the spirit and scope of the invention.

Example 1: IV Sotalol

A subject with a QTc interval of 405 msec is to receive 80 mg of oral sotalol hydrochloride by mouth twice a day (PO BID) with a steady state serum concentration reached in 3-5 days with a steady state $C_{max}$ of 800 ng/mL. With the relationship of QTc to serum concentration on average of 0.024:

$$QTc\ max = QTc\ baseline + (0.024 \times 800\ ng/mL)$$

$$= 424\ msec^*$$

Dose Initiation: To attenuate the time required to achieve steady state $C_{max}$, one can administer sotalol hydrochloride IV as an infusion. For example, 55 mg (projected to equate to 80 mg by mouth twice a day) of IV sotalol hydrochloride can be administered over 1-2 hours, the steady state $C_{max}$ estimated for an average person's serum sotalol concentration 800 ng/mL would be achieved, which would transpose to a QTc prolongation of an average of 427 msec.

*Within the prescribed FDA guideline of remaining under a maximum QTc of 500 msec.

Example 2: IV Sotalol

A subject with an initial QTc of 405 msec (average for a 70 kg person) starts receiving a sotalol hydrochloride IV infusion of 55 mg/mL and after 45 minutes the QTc is measured to be 456 msec. The infusion can be halted and the dose of sotalol hydrochloride selected for chronic administration can be reduced, the dosing interval can be prolonged, or the physician can decide not to use sotalol hydrochloride and instead turn to an alternative anti-arrhythmic therapy.

IV loading could safely expose the subject to the expected maximum sotalol hydrochloride concentration and thus maximum QTc prolongation that would be expected to occur with chronic dosing. If under observation, the QTc prolongs to a significantly greater degree, the infusion can be stopped, the dose reduced, or the subject deemed too sensitive to sotalol hydrochloride dosing and another antiarrhythmic drug could be evaluated for efficacy and safety in that particular subject. This approach would be a major safety factor for subjects, since with oral loading or oral and IV loading, the absorption continues once a pill is taken and the overshoot in QTc will continue, placing the subject at greater risk. An infusion thus provides greater safety, since the infusion can be stopped with no further significant increase in QTc.

Example 3: IV Sotalol

A 70 kg subject presents with intermittent atrial fibrillation (AF). His physician wants to place the subject on oral sotalol hydrochloride 80 mg PO BID. He has never taken sotalol before. He is admitted to the hospital and receives an infusion of IV sotalol hydrochloride (55 mg) over 1 hour. This infusion achieves a target serum concentration of 800 ng/mL. Following the infusion the QTc is checked 30 minutes after administration. If the QTc is within guidelines (less than 20% increase, or under 500 msec) an interval of 2-6 hours is left to elapse to reach the predicted trough and then 80 mg orally is given to subject, which will predictably peak in 2-4 hours and QTc will be measured again hourly (at 4-5 hours). If QTc is within guidelines, then dosing will continue orally, 80 mg every 12 hours.

The subject will thus have been exposed to a serum sotalol hydrochloride concentration predicted to be reached with chronic dosing (predicted $C_{max}$) twice in the 16 hours of observation and can be discharged safely in 24 hours knowing that the QTc will not at maximum predicted concentration exceed guidelines. Thus, in a timeframe of between 6-23 hours, sotalol hydrochloride could be fully evaluated for repolarization safety with the maximum QTc expected at a given chronic dose.

That some subjects respond unpredictably to sotalol hydrochloride, or other QT prolonging drugs is well-known. This can be explained in the case of sotalol hydrochloride by an abnormality in the potassium channel. Genetic conditions can cause mild abnormalities in protein structure of the potassium channel. These abnormalities can be dormant and only seen as marked QT prolongation when subjects are exposed to a potassium channel blocker such as sotalol hydrochloride. In these subjects with a channelopathy, the QTc may markedly increase with ensuing life threatening ventricular arrhythmias and possibly sudden cardiac death. Having a way to rapidly access the QTc effect of sotalol hydrochloride by administering an intravenous infusion when the drug administration could be halted at any time will greatly enhance subject safety. As can be seen in FIG. 1, the exposure to sotalol through an IV infusion over several hours can achieve steady state $C_{max}$ and the maximum QTc in a short period of time (less than 24 hours). Thus, permitting evaluation in hospital over 24 hours as opposed to the 3 day hospitalization currently needed to achieve steady state $C_{max}$ levels with oral sotalol hydrochloride dosing.

Another critical factor in the dosing of sotalol hydrochloride to observe maximum QTc effect is the relation of the serum concentration and QTc prolongation based on time. The phenomenon is called hysteresis: the delay between a change in a marker affected by an exposure to an agent causing its change. This can be due to delay of the drug reaching the receptor or channel or changes in the receptor or channel needed over time to be fully expressed. Information on sotalol concentration and QTc prolongation is known from the work of Somberg and colleagues. In Somberg, J. C., et al., *Am J. Ther.* 17(4):365-72 (2010). 15 normal individuals received sotalol hydrochloride infused intravenously and then at a later date administered orally. The infusion was over a 2.5 hour duration and thus the serum concentration would be at a maximum at the end of infusion (2.5 hours). The maximum QTc was seen at 2.25 hours. Thirty minutes later at hour 3, the QTc had decreased. Thus, the hysteresis between sotalol hydrochloride concentration and QTc cannot be longer than 30 minutes. Therefore, a period of 30 minutes is recommended to observe the maximum QTc effect after the completion of the infusion, to observe and then act upon the maximum QTc observed.

Dose Escalation

Figure 2:
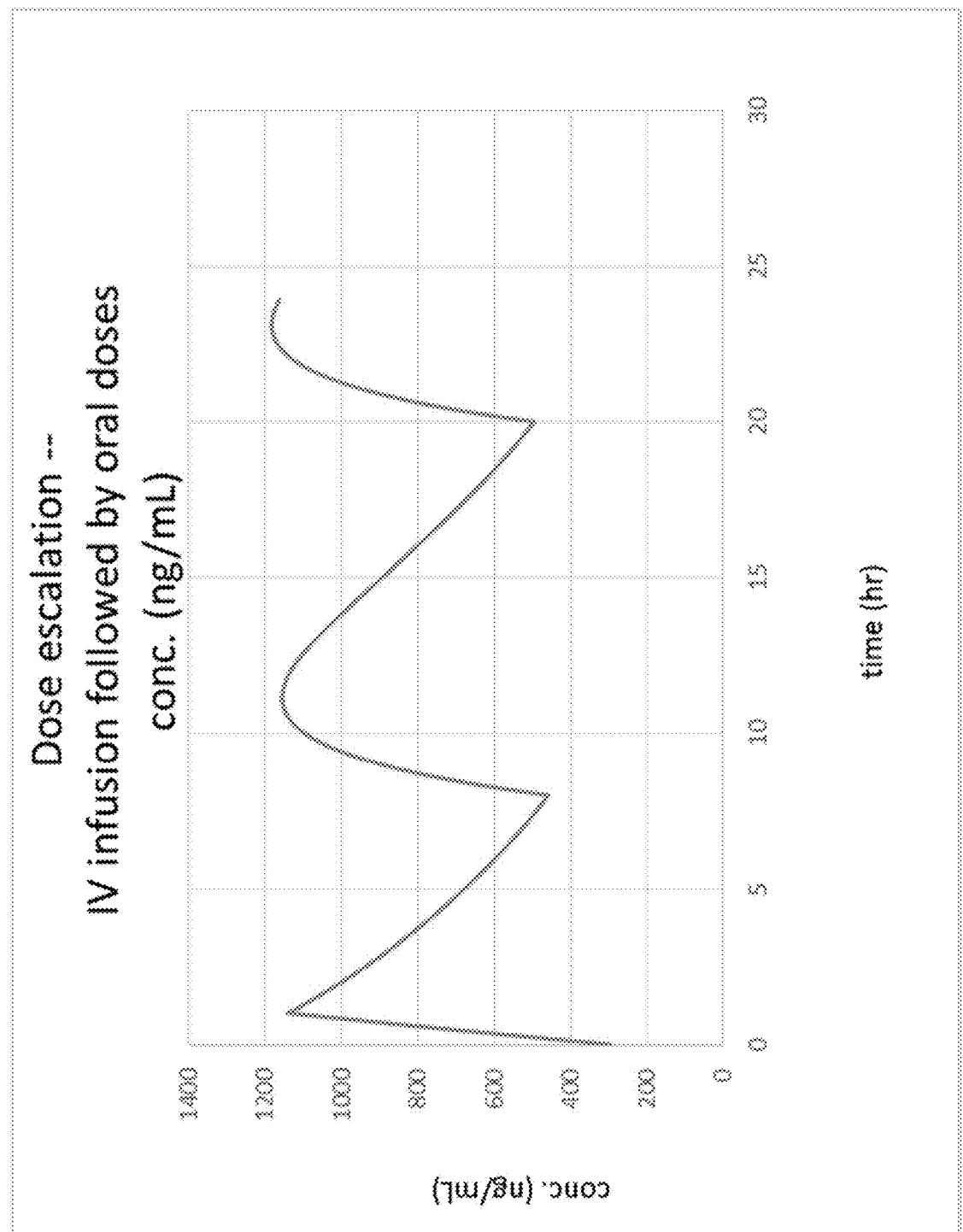
FIG. 2 is a line graph depicting dose escalation from 80 mg twice a day to 120 mg twice a day of oral sotalol hydrochloride via the intravenous administration of 55 mg of sotalol hydrochloride in 1 hour.

In an analogous manner a subject on a maintenance dose of 80 mg PO BID sotalol hydrochloride, or 120 mg PO BID could be increased to the next standard increment in oral dosing. A subject could be brought in to the hospital at the time before the next dosing interval, nadir of serum concentration, and administered an infusion over 1-2 hours of IV sotalol hydrochloride to attain the projected next highest concentration level (steady state $C_{max}$) and thus the maximum concentration the subject would be exposed to, resulting in the maximum QTc predicted exposure. This could be done in hospital in less than 24 hours such that the full risk to the subject of that serum sotalol hydrochloride concentration could be observed as shown in FIG. 2. If arrhythmias occur, cardiac resuscitation measures could be initiated, offering the subject maximal safety. If the infusion is given intravenously, the infusion could be terminated if the QTc increases beyond acceptable parameters recommended by FDA in the sotalol hydrochloride product label.

Example 4: IV Sotalol

A subject on 80 mg PO BID is brought to hospital at end of dosing interval before the next oral dose and then, receives an IV infusion of sotalol hydrochloride. Trough concentration of sotalol hydrochloride given at 80 mg PO BID can be estimated to be 400 ng/mL. The steady state $C_{max}$ of a 120 mg PO BID dose would be 1200 ng/mL. Thus, an infusion of 55 mg sotalol hydrochloride would achieve a target concentration of approximately 1200 ng/mL, exposing the subject to the maximal predicted QTc prolongation in 2 hours or less. In both the initiating and loading periods one may then proceed to continue oral dosing after a preset interval (2-6 hours) to continue sotalol hydrochloride exposure to provide anti-arrhythmic action during the transition from IV to oral drug administration.

While the methods have been described in terms of what are presently considered to be practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar embodiments. This disclosure includes any and all embodiments of the following claims.

Having now fully described this invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference herein in their entirety.

What is claimed:

1. A method of initiating oral sotalol hydrochloride therapy comprising:
   identifying a subject as naïve to sotalol, having symptomatic atrial fibrillation or atrial flutter, and currently in sinus rhythm;
   administering to the subject a single intravenous (IV) dosage of sotalol hydrochloride, over a period of 1 hour, wherein the single IV dosage comprises an amount of sotalol hydrochloride in the range of 116-141 mg;
   after completion of the single IV dosage of sotalol hydrochloride, administering a first oral dosage of sotalol hydrochloride in the amount of 120 mg.

2. The method of claim 1, wherein the first oral dosage is administered starting 4-6 hours after completion of the IV dosage.

3. The method of claim 2, further comprising administering a second oral dosage, wherein the second oral dosage is administered 12 hours after the first oral dosage.

4. The method of claim 3, further comprising administering one or more subsequent oral dosage at a 12-hour interval from the second oral dosage.

5. The method of claim 1, wherein the single IV dosage comprises an amount of sotalol hydrochloride in the range of 121-141 mg.

* * * * *